United States Patent
Miesel et al.

(10) Patent No.: US 6,248,080 B1
(45) Date of Patent: Jun. 19, 2001

(54) INTRACRANIAL MONITORING AND THERAPY DELIVERY CONTROL DEVICE, SYSTEM AND METHOD

(75) Inventors: Keith A. Miesel, St. Paul; Lee Stylos, Stillwater, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/299,774

(22) Filed: Apr. 26, 1999

Related U.S. Application Data

(63) Continuation-in-part of application No. 09/182,971, filed on Oct. 30, 1998, and a continuation-in-part of application No. 09/182,972, filed on Oct. 30, 1998, and a continuation-in-part of application No. 09/182,863, filed on Oct. 30, 1998, and a continuation-in-part of application No. 09/182,970, filed on Oct. 30, 1998, and a continuation-in-part of application No. 09/182,764, filed on Oct. 30, 1998, and a continuation-in-part of application No. 08/923,079, filed on Sep. 3, 1997, now Pat. No. 5,902,326.

(51) Int. Cl.⁷ ........................................................ A61B 5/03
(52) U.S. Cl. ............................................ 600/561; 600/311
(58) Field of Search .................................... 600/561, 311

(56) References Cited

U.S. PATENT DOCUMENTS

H1114  12/1992  Schweitzer et al. .
3,669,094  6/1972  Heyer .

(List continued on next page.)

FOREIGN PATENT DOCUMENTS

WO 80/01620  8/1980  (WO) .

*Primary Examiner*—Carl H. Layno
(74) *Attorney, Agent, or Firm*—Girma Wolde-Michael; Harold R. Patton

(57) ABSTRACT

An implantable medical device having an hermetically sealed enclosure housing electrical and electronic circuitry and a battery for powering such circuitry is connected to an intracranial lead or pigtail which measures or senses intracranial physiologic signals such as intracranial fluid pressure and/or temperature. The implantable medical device is preferably implanted subcutaneously beneath a patient's skin and telemeters stored data or real-time-sensed data to an external device which may be configured to combine barometric pressure data with intracranial pressure data to derive intracranial gage pressure. The implantable medical device and its associated lead reduce the risk of intracranial infections.

14 Claims, 15 Drawing Sheets

U.S. PATENT DOCUMENTS

| | | |
|---|---|---|
| 3,746,087 | 7/1973 | Lavering et al. . |
| 3,847,483 | 11/1974 | Shaw et al. . |
| 4,114,604 | 9/1978 | Shaw et al. . |
| 4,202,339 | 5/1980 | Wirtzfeld et al. . |
| 4,246,908 | 1/1981 | Inagaki et al. . |
| 4,281,666 | 8/1981 | Cosman . |
| 4,281,667 | 8/1981 | Cosman . |
| 4,399,820 | 8/1983 | Wirtzfeld et al. . |
| 4,407,296 | 10/1983 | Anderson . |
| 4,421,386 | 12/1983 | Podgorski . |
| 4,444,498 | 4/1984 | Heinemann . |
| 4,467,807 | 8/1984 | Bornzin . |
| 4,471,786 | 9/1984 | Inagaki et al. . |
| 4,519,401 | 5/1985 | Ko et al. . |
| 4,523,279 | 6/1985 | Sperinde et al. . |
| 4,554,927 | 11/1985 | Fussell . |
| 4,564,022 | 1/1986 | Rosenfeld . |
| 4,600,013 | 7/1986 | Landy . |
| 4,621,647 | 11/1986 | Loveland . |
| 4,623,248 | 11/1986 | Sperinde . |
| 4,651,741 | 3/1987 | Passafaro . |
| 4,677,985 | 7/1987 | Bro et al. . |
| 4,697,593 | 10/1987 | Evans et al. . |
| 4,727,879 | 3/1988 | Liess et al. . |
| 4,730,389 | 3/1988 | Baudino et al. . |
| 4,730,622 | 3/1988 | Cohen . |
| 4,738,267 | 4/1988 | Lazorthes et al. ........... 600/561 |
| 4,750,495 | 6/1988 | Moore et al. . |
| 4,791,935 | 12/1988 | Baudino et al. . |
| 4,796,641 | 1/1989 | Mills et al. . |
| 4,807,629 | 2/1989 | Baudino et al. . |
| 4,807,632 | 2/1989 | Liess et al. . |
| 4,813,421 | 3/1989 | Baudino et al. . |
| 4,815,469 | 3/1989 | Cohen et al. . |
| 4,827,933 | 5/1989 | Koning et al. . |
| 4,830,488 | 5/1989 | Heinze et al. . |
| 4,846,191 | 7/1989 | Brockway et al. . |
| 4,858,619 | 8/1989 | Toth . |
| 4,877,032 | 10/1989 | Heinze et al. . |
| 4,903,701 | 2/1990 | Moore et al. . |
| 4,967,755 | 11/1990 | Pohndorf . |
| 4,971,061 | 11/1990 | Kageyama et al. . |
| 4,984,567 | 1/1991 | Kageyama . |
| 4,995,401 | 2/1991 | Benugin et al. . |
| 5,005,573 | 4/1991 | Buchanan . |
| 5,040,538 | 8/1991 | Mortazavi . |
| 5,052,388 | 10/1991 | Sivula et al. . |
| 5,058,586 | 10/1991 | Heinze . |
| 5,067,960 | 11/1991 | Grandjean . |
| 5,074,310 | 12/1991 | Mick . |
| 5,113,862 | 5/1992 | Mortazavi . |
| 5,117,835 | 6/1992 | Mick . |
| 5,117,836 | 6/1992 | Millar . |
| 5,176,138 | 1/1993 | Thacker . |
| 5,191,898 | 3/1993 | Millar . |
| 5,199,428 | 4/1993 | Obel et al. . |
| 5,267,564 | 12/1993 | Barcel et al. . |
| 5,275,171 | 1/1994 | Barcel . |
| 5,291,899 | 3/1994 | Watanabe et al. . |
| 5,312,454 | 5/1994 | Roline et al. . |
| 5,324,326 | 6/1994 | Lubin . |
| 5,325,865 | 7/1994 | Beckman et al. . |
| 5,329,922 | 7/1994 | Atlee, III . |
| 5,342,406 | 8/1994 | Thompson . |
| 5,358,519 | 10/1994 | Grandjean . |
| 5,377,524 | 1/1995 | Wise et al. . |
| 5,411,532 | 5/1995 | Mortazavi . |
| 5,438,987 | 8/1995 | Thacker et al. . |
| 5,490,323 | 2/1996 | Thacker et al. . |
| 5,517,998 * | 5/1996 | Madison ............... 600/473 |
| 5,535,752 | 7/1996 | Halperin et al. . |
| 5,556,421 | 9/1996 | Prutchi et al. . |
| 5,564,434 | 10/1996 | Halperin et al. . |
| 5,593,430 | 1/1997 | Renger . |
| 5,601,611 | 2/1997 | Fayram et al. . |
| 5,617,873 | 4/1997 | Yost et al. . |
| 5,683,422 | 11/1997 | Rise . |
| 5,716,377 | 2/1998 | Rise . |
| 5,743,267 | 4/1998 | Nikolic et al. . |
| 5,752,976 | 5/1998 | Duffin et al. . |
| 5,758,652 | 6/1998 | Nikolic et al. . |
| 5,788,647 | 8/1998 | Eggers . |
| 5,792,186 | 8/1998 | Rise et al. . |
| 5,810,735 | 9/1998 | Halperin et al. . |
| 5,833,709 | 11/1998 | Rise et al. . |
| 5,873,840 | 2/1999 | Neff . |
| 5,904,708 | 5/1999 | Goedeke . |
| 6,113,553 * | 9/2000 | Chubbuck ............... 600/561 |
| B1 4,467,807 | 6/1992 | Bornzin . |

* cited by examiner

INTRACRANIAL MONITORING AND THERAPY DELIVERY CONTROL DEVICE, SYSTEM AND METHOD

CROSS-REFERENCE TO RELATED APPLICATIONS

This patent application is a continuation-in-part of U.S. patent application Ser. No. 08/923,079 to Lessar et al. filed Sep. 3, 1997 now U.S. Pat. No. 5,902,326, and is also a continuation-in-part of each of U.S. patent application Ser. Nos. 09/182,971; 09/182,972; 09/182,863; 09/182,970; and 09/182,764, all to Miesel et al. and filed Oct. 30, 1998, all the foregoing patent applications being hereby incorporated by reference herein, each in its respective entirety.

FIELD OF THE INVENTION

The present invention relates generally to implantable physiologic sensors, and more particularly to intracranial sensors, systems and methods.

BACKGROUND OF THE INVENTION

Implantable medical devices (IMDs) for cardiac monitoring or for delivering therapy typically include one or more sensors positioned in a patient's blood vessel, heart chamber or other portion of the body. Examples of IMDs include heart monitors, therapy delivery devices, pacemakers, implantable pulse generators (IPGs), pacer-cardio-defibrillators (PCDs), implantable cardio-defibrillators (ICDs), cardiomyo-stimulators, nerve stimulators, gastric stimulators, brain stimulators and drug delivery devices. In a cardiac therapy or monitoring context, such IMDs generally include electrodes for sensing cardiac events of interest and sense amplifiers for recording or filtering sensed events. In many currently available IMDs, sensed events such as P-waves and R-waves are employed to control the delivery of therapy in accordance with an operating algorithm. Selected electrogram (EGM) signal segments and sense event histogram data and the like are typically stored in IMD RAM for transfer to an external programmer by telemetric means at a later time.

Efforts have also been made to develop implantable physiologic signal transducers and sensors for monitoring a physiologic condition other than, or in addition to, an EGM, to thereby control delivery of a therapy, or to filter or store data.

In respect of cardiac monitoring, sensing and recording such additional physiologic signals as blood pressure, blood temperature, pH, blood gas type and blood gas concentration signals has been proposed.

One type of ideal physiologic sensor provides information concerning a patient's exercise level or workload and operates in closed loop fashion. In other words, such an ideal physiologic sensor operates to minimize divergence from an ideal operating point or set of points. Blood oxygen saturation provides a direct indication of the amount oxygen consumed by a patient when exercising. In a rate responsive pacing context, oxygen saturation is generally inversely related to pacing rate. That is, as oxygen saturation decreases due to exercise, pacing rates are correspondingly increased so that divergence from the optimum operating point is minimized. In such a fashion a closed loop system capable of monitoring a physiologic parameter and delivering an appropriate therapy is implemented.

Piezoresistive pressure transducers mounted at or near the distal tips of catheters have been employed in such pressure monitoring applications. U.S. Pat. No. 4,023,562 describes a piezoresistive bridge of four, orthogonally disposed, semiconductor strain gauges formed interiorly on a single crystal silicon diaphragm area of a silicon base. A protective silicon cover is bonded to the base around the periphery of the diaphragm area to form a sealed, evacuated chamber. Deflection of the diaphragm due to ambient pressure changes is detected by the changes in resistance of the strain gauges.

Because the change in resistance is so small, a high current is required to detect the voltage change due to the resistance change. The high current requirements render the piezoresistive bridge unsuitable for long term use with an implanted power source. High gain amplifiers that are subject to drift over time are also required to amplify the resistance-related voltage change.

Other semiconductor sensors employ CMOS IC technology in the fabrication of pressure responsive silicon diaphragm bearing capacitive plates that are spaced from stationary plates. The change in capacitance due to pressure waves acting on the diaphragm is measured, typically through a bridge circuit, as disclosed, for example, in the article "A Design of Capacitive Pressure Transducer" by Ko et al., in *IEEE Proc. Symp. Biosensors*, 1984, p.32. Again, fabrication for long term implantation and stability is complicated.

In addition, differential capacitive plate, fluid filled pressure transducers employing thin metal or ceramic diaphragms have also been proposed for large scale industrial process control applications as disclosed, for example, in the article "A ceramic differential-pressure transducer" by Graeger et al., *Philips Tech. Rev.*, 43:4:86–93, February 1987. The large scale of such pressure transducers does not lend itself to miniaturization for chronic implantation.

Efforts have been underway for years to develop pressure transducers and sensors for temporary or chronic use in a body organ or vessel, including those relating to the measurement or monitoring of intracranial fluid pressure. Many different designs and operating systems have been proposed and placed into temporary or chronic use with patients.

Patients suffering from head trauma, adult head trauma and infantile hydrocephalus and attendant increased intracranial fluid pressure are often difficult to treat successfully. Among other things, this is because the sensors generally employed to sense intracranial pressure often provide a direct path for infectious agents to enter the brain (leading to dangerous intracranial infections), the actual source or cause of the increased intracranial pressure is poorly understood or not understood at all, or the devices and methods employed to sense intracranial pressure are limited in their capabilities, the locations where they may be positioned, or the durations of time over which they may be used.

Various implementations of systems for sensing physiologic parameters are known in the art. Some examples of such sensors and associated methods of sensing may be found in at least some of the patents, patent applications or publications listed in Table 1 below.

TABLE 1

| U.S. Pat. No., U.S. patent application Ser. No. or Document No. | Inventor(s) | Issue/ Publication/ Filing Date |
|---|---|---|
| WO 80/01620 | Kraska et al. | August 7, 1980 |
| H1114 | Schweitzer et al. | December 1, 1992 |
| B1 4,467,807 | Bornzin | June 30, 1992 |
| 3,669,094 | Heyer | June 13, 1972 |
| 3,746,087 | Lavering et al. | July 17, 1973 |
| 3,847,483 | Shaw et al. | November 12, 1974 |
| 4,114,604 | Shaw et al. | September 19, 1978 |
| 4,202,339 | Wirtzfeld et al. | May 13, 1980 |
| 4,246,908 | Inagaki et al. | January 27, 1981 |
| 4,287,667 | Cosman | August 4, 1981 |
| 4,399,820 | Wirtzfeld et al. | August 23, 1983 |
| 4,407,296 | Anderson | October 4, 1983 |
| 4,421,386 | Podgorski | December 20, 1983 |
| 4,444,498 | Heinemann | April 24, 1984 |
| 4,471,786 | Inagaki et al. | September 18, 1984 |
| 4,467,807 | Bornzin | August 28, 1984 |
| 5,519,401 | Ko et al. | May 28, 1985 |
| 4,523,279 | Sperinde et al. | June 11, 1985 |
| 4,564,022 | Rosenfeld | January 14, 1986 |
| 4,554,977 | Fussell | November 26, 1985 |
| 4,600,013 | Landy | January 15, 1986 |
| 4,621,647 | Loveland | November 11, 1986 |
| 4,623,248 | Sperinde | November 18, 1986 |
| 4,677,985 | Bro et al. | July 7, 1985 |
| 4,651,741 | Passafaro | March 24, 1987 |
| 4,697,593 | Evans et al. | October 6, 1987 |
| 4,727,879 | Liess et al. | March 1, 1988 |
| 4,730,389 | Baudino et al. | March 15, 1988 |
| 4,730,622 | Cohen | March 15, 1988 |
| 4,783,267 | Lazorthes et al. | April 19, 1988 |
| 4,750,495 | Moore et al. | June 14, 1988 |
| 4,791,935 | Baudino et al. | December 20, 1988 |
| 4,796,641 | Mills et al. | January 10, 1989 |
| 4,807,629 | Baudino et al. | February 28, 1989 |
| 4,807,632 | Liess et al. | February 28, 1989 |
| 4,813,421 | Baudino et al. | March 21, 1989 |
| 4,815,469 | Cohen et al. | March 28, 1989 |
| 4,827,933 | Koning et al. | May 9, 1989 |
| 4,858,619 | Toth | August 22, 1989 |
| 4,830,488 | Heinze et al. | May 16, 1989 |
| 4,846,191 | Brockway et al. | July 5, 1994 |
| 4,877,032 | Heinze et al. | October 31, 1989 |
| 4,903,701 | Moore et al. | February 27, 1990 |
| 4,967,755 | Pohndorf | November 6, 1990 |
| 4,971,061 | Kageyama et al. | November 20, 1990 |
| 4,984,567 | Kageyama | January 15, 1991 |
| 4,995,401 | Benugin et al. | February 26, 1991 |
| 5,005,573 | Buchanan | April 9, 1991 |
| 5,040,538 | Mortazavi | August 20, 1991 |
| 5,052,388 | Sivula et al. | October 1, 1991 |
| 5,058,586 | Heinze | October 22, 1991 |
| 5,074,310 | Mick | December 24, 1991 |
| 5,067,960 | Grandjean | November 26, 1991 |
| 5,117,835 | Mick | June 2, 1992 |
| 5,113,862 | Mortazavi | May 19, 1992 |
| 5,117,836 | Millar | June 2, 1992 |
| 5,176,138 | Thacker | January 5, 1993 |
| 5,191,898 | Millar | March 9, 1993 |
| 5,199,428 | Obel et al. | April 6, 1993 |
| 5,267,564 | Barcel et al. | December 7, 1993 |
| 5,275,171 | Barcel | January 4, 1994 |
| 5,291,899 | Watanabe et al. | March 8, 1994 |
| 5,312,454 | Roline et al. | May 17, 1994 |
| 5,324,326 | Lubin | June 28, 1994 |
| 5,325,865 | Beckman et al | July 5, 1994 |
| 5,329,922 | Atlee, III | July 19, 1994 |
| 5,342,406 | Thompson | August 30, 1994 |
| 5,358,519 | Grandjean | October 25, 1994 |
| 5,377,524 | Wise et al. | January 3, 1995 |
| 5,411,532 | Mortazavi | May 2, 1995 |
| 5,438,987 | Thacker et al. | August 8, 1995 |
| 5,490,323 | Thacker et al. | February 13, 1996 |
| 5,535,752 | Halperin et al. | July 16, 1996 |
| 5,564,434 | Halperin et al. | October 15, 1996 |

TABLE 1-continued

| U.S. Pat. No., U.S. patent application Ser. No. or Document No. | Inventor(s) | Issue/ Publication/ Filing Date |
|---|---|---|
| 5,556,421 | Prutchi et al. | September 17, 1996 |
| 5,593,430 | Renger | January 14, 1997 |
| 5,601,611 | Fayram et al. | February 11, 1997 |
| 5,617,873 | Yost et al. | April 8, 1997 |
| 5,683,422 | Rise | November 4, 1997 |
| 5,716,377 | Rise | February 10, 1998 |
| 5,743,267 | Nikolic et al. | April 28, 1998 |
| 5,752,976 | Duffin et al. | May 19, 1998 |
| 5,758,652 | Nikolic et al. | June 2, 1998 |
| 5,788,647 | Eggers | August 4, 1998 |
| 5,792,186 | Rise et al. | August 11, 1998 |
| 5,810,735 | Halperin et al. | May 1, 1997 |
| 5,833,709 | Rise et al. | November 10, 1998 |
| 5,873,840 | Neff | February 23, 1999 |
| 09/044,613 | Goedeke | March 19, 1998 (filing date) |

All patents, patent applications and publications listed in Table 1 hereinabove are hereby incorporated by reference herein, each in its respective entirety. As those of ordinary skill in the art will appreciate readily upon reading the Summary of the Invention, the Detailed Description of the Various Embodiments, and the claims set forth below, at least some of the devices and methods disclosed in the patents of listed herein may be modified advantageously in accordance with the teachings of the present invention.

SUMMARY OF THE INVENTION

The present invention has certain objects. That is, various embodiments of the present invention provide solutions to one or more of the following problems existing in the prior art with respect to intracranial physiologic sensors: (a) intracranial sensors which are incapable of providing accurate intracranial absolute fluid pressure data over extended periods of time; (b) intracranial sensors which are incapable of providing accurate intracranial gage fluid pressure data over extended periods of time; (c) intracranial sensors which are incapable of providing intracranial temperature data; (d) intracranial sensors that provide direct paths for external infectious agents to enter the brain; (e) intracranial fluid pressure sensors that exhibit excessive rates of output signal drift; (f) intracranial fluid pressure sensors that require constant or regular re-calibration; (g) intracranial fluid pressure sensors that must be removed from the patient for re-calibration or testing; (h) intracranial fluid pressure sensors that provide different pressure readings solely in response to the patient's physical position and/or elevation changing; (i) intracranial sensors and systems which require the patient to remain in a fixed stationary position; (i) intracranial sensors and systems which do not directly measure intracranial fluid pressure; (j) intracranial fluid pressure sensors that degrade or whose physical characteristics change over time following implantation within the body; (k) intracranial sensors which must be connected to an external module or device located outside the patient and not implanted therein; (k) intracranial pressure sensor(s) that is (are) incapable of providing data that may be used to accurately and consistently diagnose and identify the actual source or cause of excessive intracranial pressure; (l) intracranial fluid pressure sensors that must be placed or located within or near subarachnoid spaces; (m) intracranial fluid pressure sensors that provide readings or measurements that must be physically checked by a nurse or physician on an on-going, continuous basis; (n) intracranial fluid pressure sensors and systems that are incapable of permitting dangerous changes in intracranial fluid pressure to be detected and diagnosed quickly enough to permit delivery of an appropriate therapy prior to the onset of cerebral ischemia. Various embodiments of the present invention have the object of solving at least one of the foregoing problems.

In comparison to known intracranial sensors, systems and methods, various embodiments of the present invention may provide one or more of the following advantages: (a) providing an intracranial pressure sensor which exhibits little or no drift in the output signals generated thereby, even over extended periods of time; (b) providing an intracranial sensor and system capable of measuring intracranial pressure directly; (c) providing one or more intracranial sensors and system capable of measuring either or both of intracranial fluid pressure and intracranial temperature; (d) substantially reducing the risk of intracranial infection; (e) permitting intracranial pressure to be monitored over extended periods of time with substantially reduced risk of infection; (f) permitting a patient to self-monitor intracranial physiologic parameters such as intracranial fluid pressure and intracranial temperature; (g) permitting the intracranial parameters of a patient such as intracranial pressure and intracranial temperature to be monitored remotely; (h) permitting long term intracranial therapy to be automatically provided to a patient in a manner similar to patients discharged from a hospital following a pacemaker implant; (i) permitting a patient to have increased mobility, even while intracranial physiologic parameters are being measured; (j) reducing delays in diagnosing or detecting dangerous changes in intracranial fluid pressure or temperature; (k) reducing delays in delivering an appropriate therapy to a patient suffering from head trauma, hydrocephalus, or intracranial infection; (l) alerting the patient, physician or nurse automatically when a predetermined threshold for an intracranial physiologic parameter measured by an intracranial sensor is met, exceeded or dropped below; (m) continuously monitoring and storing intracranial sensor data within an implantable medical device for subsequent or contemporaneous retrieval or telemetry; (n) reducing the amount of time nurses or physicians must devote to monitoring intracranial fluid pressure measurements or status; (o) reducing health care costs; (p) improving outcomes for patients suffering from head trauma, hydrocephalus, or intracranial infection; (q) permitting intracranial physiologic parameters such as intracranial fluid pressure and temperature to be sensed or measured at locations other than the subarachnoid spaces, such as within one or more of the cerebral ventricles as well as within brain tissue itself; (r) permitting practically instantaneous and appropriate therapy to be delivered to the brain in response to a predetermined condition being detected; (s) permitting an appropriate therapy to be delivered to that region of the brain where therapy should optimally be provided in response to a predetermined condition being detected; (t) implantably sensing physiologic parameters such as intracranial pressure and/or intracranial temperature at a plurality of locations within, around or near the brain to permit more accurate diagnosis and treatment of cerebral symptoms in a patient.

Some embodiments of the invention include one or more of the following features or corresponding methods of delivering therapy, making, using or implanting same: (a) an integrated implantable medical device system comprising at least one temperature and/or pressure sensor lead implanted within or near the brain and connected to a corresponding IMD which receives and stores and/or transmits to an external device the signals sensed and generated thereby; (b) an integrated implantable medical device system comprising a plurality of temperature and/or pressure sensors lead implanted within or near the brain and connected to a corresponding IMD which receives and stores and/or transmits to an external device the signals sensed and generated thereby; (c) an implantable intracranial pressure and/or temperature sensor which exhibits little or no drift in the output signals generated thereby; (d) an implantable intracranial pressure and/or temperature sensor lead configured for positioning the pressure and/or temperature sensor thereof in a subarachnoid space; (e) an implantable intracranial pressure sensor configured for positioning the pressure and/or temperature sensor thereof in one or more of the cerebral ventricles, such as the lateral, third and/or fourth ventricles; (f) an implantable intracranial pressure and/or temperature sensor configured for positioning directly within brain tissue; (g) an implantable intracranial pressure sensor having a sheath or other protective cover disposed over at least a portion of the pressure sensing diaphragm or surface thereof; (h) an implantable intracranial pressure sensor having a biocompatible and/or biostable metallic surface forming at least a portion of the pressure sensing diaphragm or surface thereof; (i) an implantable intracranial pressure sensor having a biocompatible and/or biostable metallic member disposed over or bonded to the active or actual pressure sensing mechanism and/or electronics thereof; (j) an integrated implantable medical device system comprising one or more temperature and/or pressure sensor leads implanted within or near the brain and connected to a corresponding IMD which receives and/or transmits to an external device the signals sensed and generated thereby, upon the presence of a predetermined condition or state being detected or sensed within or near the brain, the IMD, the external device or other device providing or causing the delivery of an appropriate therapy, the appropriate therapy comprising one or more of opening one or more cerebral-spinal fluid ("CSF") valves or shunts located within or near the brain, closing one or more CSF valves or shunts located within or near the brain, delivering one or more of an antibiotic, an antiviral agent, an anti-inflammatory agent, a vaccine and a drug to a preselected site within or near the brain; (k) an integrated implantable medical device system comprising one or more temperature and/or pressure sensor leads implanted within or near the brain and connected to a corresponding IMD which receives and/or transmits to an external device the signals sensed and generated thereby, upon the presence of a predetermined condition or state being detected or sensed within or near the brain, the IMD, the external device or other device providing or causing an electronic or audio alert or alarm to be generated locally or remotely; (I) an integrated implantable medical device system comprising one or more temperature and/or pressure sensor leads implanted within or near the brain and connected to a corresponding IMD which receives, stores and/or transmits to an external device the signals sensed and generated thereby, the IMD being capable of communicating with the external or other device by electrical, telemetric, radio, infra-red, and/or other means; (m) an integrated implantable medical device system comprising one or more temperature and/or pressure sensor leads implanted within or near the brain and connected to a corresponding IMD which receives, stores and/or transmits to an external device the signals sensed and generated thereby, the IMD and/or the external or other device processing and analyzing data sensed by the sensors to determine whether or not a predetermined condition or state exists in or near the brain; (n) an integrated implantable medical device system comprising one or more temperature and/or pressure sensor leads implanted within or near the brain and connected to a corresponding IMD, the IMD being capable of communicating with and transferring data and/or information to at least one external monitoring, storage and/or processing device through electrical, telemetric, infra-red, radio, server, telephonic, satellite, and/or internet means.

The foregoing Summary of the Invention is not intended to describe each embodiment or every implementation of the present invention. Other objects, advantages and features, together with a more complete understanding of the invention, will become apparent and appreciated by referring to the following Detailed Description and claims taken in conjunction with the accompanying Drawings.

BRIEF DESCRIPTION OF THE DRAWINGS

The various embodiments of the present invention will be more readily understood by referring to the following Detailed Description of the Preferred Embodiments and the following Drawings, where like reference numerals indicate like structures.

DETAILED DESCRIPTION OF THE PREFERRED EMBODIMENTS

Figure 1A:
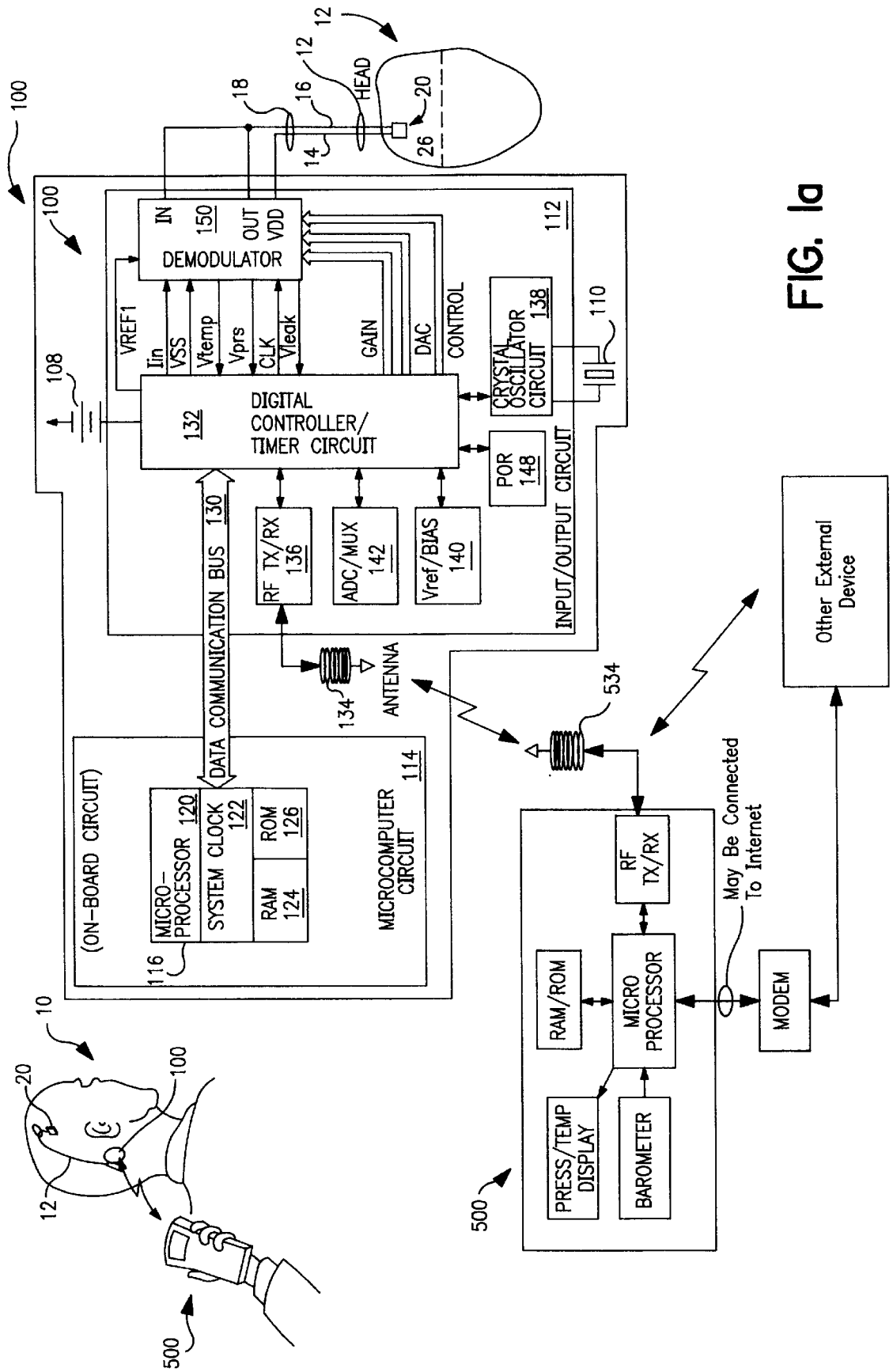
FIG. 1a is block diagram of an implantable, programmable intracranial pressure/temperature transmitter and lead system of the present invention.

The present invention relates generally to implantable intracranial physiologic sensors, systems and methods. In describing the preferred embodiments, we begin by describing some overall attributes of the components, systems and methods of the present invention, followed by describing details of some preferred embodiments of the pressure sensor of the present invention.

Referring now to FIGS. 1a through 1d, the integrated implantable system of the present invention generally comprises an implantable medical device ("IMD") 100, at least one sensor lead 12, and external device 500. IMD 100 and sensor lead 12 are implanted within a human body, while external device 500 is preferably (although not necessarily) located outside the body.

Sensor lead 12 is connected to IMD 100 and has one or more physiologic sensors connected to or incorporated into it for sensing or detecting physiologic parameters or signals originating at or near a brain such as pressure or temperature signals. Sensor lead 12 is implanted in, on or near the brain of patient 10.

IMD 100 is implanted beneath the skin of a patient, most preferably beneath the ear of patient 10. Other implantation locations for IMD 100 are also suitable, such as at the base of the neck, near the clavicle, beneath the back, and so on. Lead 12 is tunnelled beneath the skin between the location where the proximal end of lead 12 is connected to IMD 100 and the point at which the distal end of lead 12 is routed through the skull of patient 10 for placement of its sensors near, at or in the brain.

Signals sensed by the sensor(s) mounted on or attached to lead 12 are routed to IMD 100, where they may be amplified, stored and/or processed prior to being sent or relayed to external device 500.

External device 500 may receive data or information from IMD 100 through the skin of patient 10 by any of several suitable means, such as electrical, telemetric, radio, infrared, or other means well known to those skilled in the art. In preferred embodiments of the present invention, IMD 100 and external device 500 communicate with one another by telemetric means through antennae 134 and 534. Note that more than one lead 12 may be attached to IMD 100, and that leads 12 may be placed or positioned such that they measure or sense signals originating in different areas, regions or portions of the brain.

A plurality of IMD 100's and leads 12 may also be employed in the integrated implantable system of the present invention to permit or facilitate the acquisition of signals or data from different areas, portions or regions of the brain. In one embodiment of the present invention, lead 12 comprises a plurality of sensors such as one pressure sensor or one pressure/temperature sensor. In another embodiment of the present invention, lead 12 comprises a plurality or string of like sensors disposed along the length of lead 12 such that each sensor measures a physiologic parameter (e.g., pressure and/or temperature) at a location in, on or near the brain that is different from that measured or sensed by an adjoining like sensor. Thus, lead configurations other than those shown explicitly the Drawings may be practiced in conjunction with the present invention. For example, a switch matrix in IMD 100 may be employed to select an electrode or electrodes (or sensor or sensors) of lead 12 for coupling to a wide band (e.g., 0.5–200 Hz) amplifier in IMD 100 for use in subsequent digital signal analysis, storage and/or data transfer or telemetry. Selection of the electrodes or sensors is preferably controlled by microprocessor 120 via data/address bus 130, which selections may be varied as desired. Signals from the electrodes or sensors selected for coupling to a bandpass amplifier and/or demodulator 150 are provided to an appropriate multiplexer and thereafter converted to multi-bit digital signals by A/D converter 142 for storage in random access memory 124, most preferably under the control of a direct memory access circuit (not shown in the Figures). Microprocessor 120 or another micro-controller, controller or digital signal processor (DSP) may employ digital signal analysis techniques to characterize the digitized signals stored in random access memory 124 to recognize and classify the sensed intracranial signals employing any of the numerous signal processing methodologies.

IMD 100 most preferably contains a suitable source of electrical energy 108 (such as a battery) to power lead 12 and the circuitry of IMD 100. IMD 100 is also most preferably hermetically sealed and presents a biocompatible surface to tissue which surrounds it after implantation. Unlike fluid-filled catheters or other intracranial pressure sensors which are positioned in the brain and which have portions which protrude through the skull to the outside external environment, IMD 100 and lead 12 are completely implanted within patient 12, and therefore do not present any direct paths for infectious agents to follow into the brain. The integrated implanted system of the present invention thus substantially reduces the risk of intracranial infection. Additionally, fluid-filled catheters or other intracranial pressure sensors positioned in the brain and having portions which protrude through the skull to the outside external environment are often used by physicians for only two to five days because the risk of infection becomes so great that the sensors must be removed from the brain, whether or not a need still exists to monitor intracranial pressure. Contrariwise, the integrated implanted system of the present invention permits intracranial pressure to be monitored over substantially extended periods of time without increasing the risk of infection.

Lead 12 may have mounted, attached thereto or incorporated therein one or more pressure sensors, one or more temperature sensors, one or more combined pressure/temperature sensors, one or more electrically stimulating electrodes, one or more electrical sensing electrodes, one or more oxygen concentration or saturation sensors, one or more pH sensors, and one or more other suitable type of sensor.

External device 500 may receive data from IMD 100 that is relayed in real time thereto as the data are sensed by the one or more sensors disposed in lead 12. Alternatively, IMD 100 stores in memory signals received from the sensors of lead 12, and uplinks those signals to external device 500 at predetermined intervals or upon receiving a command to do so from external device 500. As shown in FIG. 1b, external device 500 may be a programmer device similar to those well known in the pacing arts for controlling and programming implantable pacemakers or PCD's which is capable of communicating by telemetric or other means with IMD 100. An exemplary embodiment of an external programmer readily adapted for use with the present invention is the commercially available Medtronic Model 9790 programmer, which is microprocessor-based and provides a series of encoded signals to IMD 100, typically through a programming head which transmits or telemeters radio-frequency (RF) encoded signals to IMD 100. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from IMD 100. For example, external device 500 may be a hand-held, pager-like or pendant-like device similar to those shown in FIGS. 1a, 1c and 1d. External device 500 may even be configured to permit a patient to self-monitor intracranial physiologic parameters such as intracranial fluid pressure and intracranial temperature. Thus, the functionality and features of external device 500 may range between being very limited in scope (e.g., permitting only the display of information uplinked from IMD 100) to being very sophisticated in scope (e.g., permitting the processing and analysis of data uplinked from IMD 100, or controlling therapy device 600 for the delivery of one or more therapies to patient 10 in response to the detection of a predetermined condition or state in the brain sensed by the one or more sensors of lead 12).

External device 500 most preferably includes means for measuring barometric or atmospheric pressure. The barometric pressure measured by external device 500 is combined with the intracranial absolute pressure measured by the sensor(s) of lead 12 to calculate the actual intracranial gage pressure, which is believed to provide a most useful diagnostic measure of intracranial fluid pressure. The calculation of gage pressure may be performed by external device 500 upon receipt of absolute pressure data from IMD 100, or conversely that calculation may be performed by IMD 100 upon receipt of atmospheric pressure data from external device 500. In still other embodiments of the present invention, barometric pressure data are provided by a device other than external device 500, and are provided to external device 500 or to IMD 100 directly. The calculation of intracranial gage pressure using barometric pressure data and intracranial absolute pressure data may also be performed by a computing device other than external device 500 or IMD 100.

The functionality and features of IMD 100 may likewise vary in sophistication, ranging between the very simple (e.g., merely powering the sensors of lead 12 and relaying information gathered therefrom to external device 500) to the very sophisticated (e.g., processing and/or storage of acquired signals by a microprocessor, controller, digital signal processor or other computing device, determining whether a predetermined condition or state exists in the brain of the patient, triggering an alarm or a therapy in response to detecting such a condition or state). It is contemplated in the present invention that some embodiments of IMD 100 may continuously monitor and store intracranial sensor data therewithin for subsequent or contemporaneous retrieval or telemetry to external device 500. IMD 100 may also control therapy device 600, or alternatively therapy device 600 may be controlled by external device 500 or another external device. It is contemplated in the present invention that long term intracranial therapy may be automatically provided to a patient under the control of IMD 100 in a manner similar to that of a patient discharged from a hospital following a pacemaker implant.

As shown in FIGS. 1a through 1d and as further explicated and embellished here, IMD 100 and/or external device 500 may be linked, connected to or communicate with still other external devices such as printers, visual displays, modems, servers, local area networks (LAN's), wide area networks (WAN's), hospital stations, remote monitoring and/or analysis computers and/or servers by telemetric, telephonic, radio, infra-red, ground station/satellite systems, and so on. It is therefore contemplated in the present invention that signals sensed by lead 12, routed through, stored, processed and/or analyzed by IMD 100, and relayed or otherwise sent to external device 500 may be subsequently routed to still other display, computing or analysis devices so that appropriate alarms may be generated, information may be remotely viewed, processed or analyzed, or appropriate therapy may be triggered, enabled or delivered to the patient.

Thus, it is contemplated in the present invention that intracranial parameters of a patient such as intracranial pressure and intracranial temperature be monitored at locations near and remote from the patient's location.

It is further contemplated in the present invention that a patient, a physician or a nurse be alerted automatically when a predetermined threshold for an intracranial physiologic parameter such as intracranial pressure or temperature measured by an intracranial sensor is met, exceeded or dropped below. For example, an integrated implantable medical device system of the present invention may comprise one or more temperature and/or pressure sensor leads 12 implanted within or near the brain and connected to corresponding IMD 100 which receives and/or transmits to external device 500 the signals sensed and generated by leads 12. Upon the sensor(s) detecting the presence of a predetermined condition or state such as excessive intracranial pressure or temperature, IMD 100, external device 500 or another device provides or causes an electronic or audio alert or alarm to be generated locally or remotely.

It is still further contemplated in the present invention that appropriate therapy be delivered to the brain by the system in response to a predetermined condition or state, such as excessive intracranial fluid pressure or temperature, being detected.

For example, an integrated implantable medical device system of the present invention comprising IMD 100, external device 500, therapy delivery device 600, and one or more temperature and/or pressure sensor leads 12 implanted within or near the brain and connected to corresponding IMD 100, IMD 100 receiving and/or transmitting to external device 500 the signals sensed and generated by lead 12, is preferably capable, upon detecting or sensing the presence of a predetermined intracranial condition or state (such as excessive intracranial fluid pressure or temperature), of having IMD 100, external device 500 and/or other external device provide or deliver an appropriate therapy, the appropriate therapy comprising one or more of opening one or more cerebral-spinal fluid ("CSF") valves or shunts located within or near the brain, closing one or more CSF valves or shunts located within or near the brain, delivering one or more of an antibiotic, an antiviral agent, an anti-inflammatory agent, a vaccine and a drug to a preselected site within or near the brain. In still other embodiments of the present invention it is contemplated that an appropriate therapy be delivered to that region of the brain where therapy should optimally be provided in response to such predetermined conditions being detected, and that physiologic parameters such as intracranial pressure and/or intracranial temperature be sensed at a plurality of locations within, around or near the brain to permit more accurate diagnosis and treatment of cerebral symptoms in a patient.

In comparison to known intracranial sensors, systems and methods, various embodiments of the present invention provide several distinct advantages. One significant advantage provided by the present invention is the provision of an intracranial pressure sensor which exhibits little or no drift in the output signals generated thereby, even over extended periods of time. In many prior art solid state intracranial pressure sensors, the drift present in the output signals they generate is of the same order of magnitude (e.g., 6–10 mm Hg) as that of the change in intracranial pressure often observed between normal healthy intracranial fluid pressure levels and those which can cause death (e.g., a change of intracranial pressure ranging between about 6 mm Hg and about 10 mm Hg). Thus, pressure sensor output signal drift is a significant problem because a physician monitoring the intracranial fluid pressure of a patient suffering from head trauma, adult hydrocephalus infantile hydrocephalus, or the like, using a prior art piezoresistive solid state fluid pressure measuring device cannot tell on the basis of pressure data alone whether observed changes in intracranial fluid pressure arise from actual changes in intracranial fluid pressure or from sensor drift.

Many times the only way to determine the nature of such changes in intracranial fluid pressure is to remove the sensor from the patient's head and see whether the sensor measures zero pressure at barometric pressure. If it does not, the sensor must be recalibrated to read zero pressure under atmospheric conditions and re-inserted into the patient's head. The intracranial pressure sensor of the present invention eliminates this problem entirely because the output signals it provides are so stable that they are calculated to drift less than 1 mm Hg over a two year period of time. Thus, a change in intracranial fluid pressure indicated by the pressure sensor of the present invention corresponds to an actual change in intracranial fluid pressure, and not to a sensor hardware problem.

The present invention also permits the amount of time nurses or physicians must devote to monitoring intracranial fluid pressure measurements or status to be reduced substantially since the system may be configured to produce an alert only when intracranial pressure or temperature reaches predetermined levels.

The significant reduction in the drift of intracranial pressure sensor signals permitted by the present invention has the additional benefit of permitting delays in diagnosing or detecting dangerous changes in intracranial fluid pressure or temperature to be reduced, or of permitting delays in delivering an appropriate therapy to a patient suffering from dangerous changes in intracranial fluid pressure or temperature to be reduced. In some circumstances those benefits of the present invention will be life-saving. Unlike prior art intracranial pressure sensors which must be placed either at or near the arachnoid spaces between the brain and the dura, or outside the dura, the pressure sensor of the present invention may be placed directly in brain tissue or even within the ventricles of the brain to thereby provide a highly accurate indication of true intracranial fluid pressure. Shielding member 75 shown in FIGS. 4 and 5, more about which we say below, prevents brain tissue from impinging directly on pressure sensing diaphragm 54 of the present invention.

In preferred embodiments of the present invention, an implantable intracranial pressure or other type of sensor has a biocompatible and/or biostable metallic surface forming at least a portion of the pressure sensing diaphragm or surface thereof. Preferred metals for forming such surfaces include titanium, nobium, tantalum, gold, platinum, stainless steel, and alloys or combinations thereof. It is also preferred that implantable intracranial pressure sensors of the present invention have a biocompatible and/or biostable metallic member disposed over or bonded to the active or actual pressure sensing mechanism and/or electronics thereof, more about which we say below.

Many, if not all, prior art intracranial fluid pressure sensors force a patient to remain in a relatively fixed position while intracranial pressure is being monitored. The present invention permits a patient the option to become ambulatory and move about, even while intracranial physiologic parameters are being measured, because no wires or tubes are attached to the patient's head to limit the patient's movements or position.

It is a significant advantage of some embodiments of the present invention that both intracranial pressure and temperature measurements are provided. This is because increases in intracranial fluid pressure may result from: (a) an increased volume of CSF being retained in the brain because an exit path for the CSF from the brain is blocked or because too much CSF is being produced, or (b) an intracranial infection is causing too much CSF to be generated within the brain. Increases in CSF volume in the brain which are infection related are usually attended by an increase in intracranial temperature. Provision of both intracranial fluid pressure and temperature data helps a physician diagnose and treat more accurately and quickly the source of the problem. Additionally, the highly site specific intracranial pressure and temperature measurements permitted by various embodiments of the present invention may reveal other important relationships yet to be discovered.

In one embodiment of the present invention, lead 12 is a capacitive pressure sensing lead and is preferably designed to chronically sense or measure intracranial fluid pressure ("ICP") over absolute pressures ranging between about 500 mm Hg and about 900 mm Hg within a frequency range of about 0 to 100 Hz. Lead 12 is preferably employed in conjunction with IMD 100, which is most preferably hermetically sealed, and includes a primary or secondary battery or capacitor for providing electrical energy to electronic and electrical circuitry disposed within hermetically sealed IMD 100.

As mentioned above, in one embodiment of the present invention IMD 100 employs a microprocessor based demodulation and telemetry system capable of telemetering out ICP data or signals to external telemetry/display device 500 as the data are acquired. In more sophisticated embodiments of the present invention, signals are sensed by lead 12 at pre-programmed intervals, stored in IMD 100, and then telemetered out to external device 500 (which may be, for example, an external programmer/transceiver) upon receipt or execution of a predetermined command in a manner largely similar to that employed currently in multi-programmable implantable pacemakers.

As discussed above, external device 500 and/or IMD 100 may include means for correlating ICP and predetermined, preprogrammed intracranial pressure limits, which if exceeded, met or dropped below cause an alarm to be sounded or actuated, either by external device 500, IMD 100 or both. The alarm may be directed to nurses or physicians at a hospital desk or in the hospital room, the patient himself, or to a remote site where the patient's intracranial pressure, temperature or other physiologic parameter is being monitored and/or analyzed. Moreover, the predetermined, preprogrammed intracranial pressure limits, which if exceeded, met or dropped below, may be employed as a feedback control system parameter to actuate the delivery or cessation of delivery of a therapy such as shunt opening or closing, valve opening or closing, drug delivery or cessation, stimulation or cessation of stimulation, monitoring of a physiologic parameter or the cessation of the monitoring of a physiologic parameter.

As mentioned above, in the general case lead 12 is implanted at some location in or near the brain where the desired physiologic parameter is to be measured. In the general case IMD 100 implanted subcutaneously in much the same manner as a pacemaker, either by tunneling the lead down subcutaneously from the top of the head to the subdlavicular region, or if device size permits, tunneling to a location adjacent to an cranial access burr hole through which lead 12 is routed, or at some location removed from the burr hole but most preferably above the neck. If sufficient volume is present within the skull to accept IMD 100, IMD may even (but less preferably) be implanted within the skull along with lead 12.

ICP System Overview

Figure 1B:
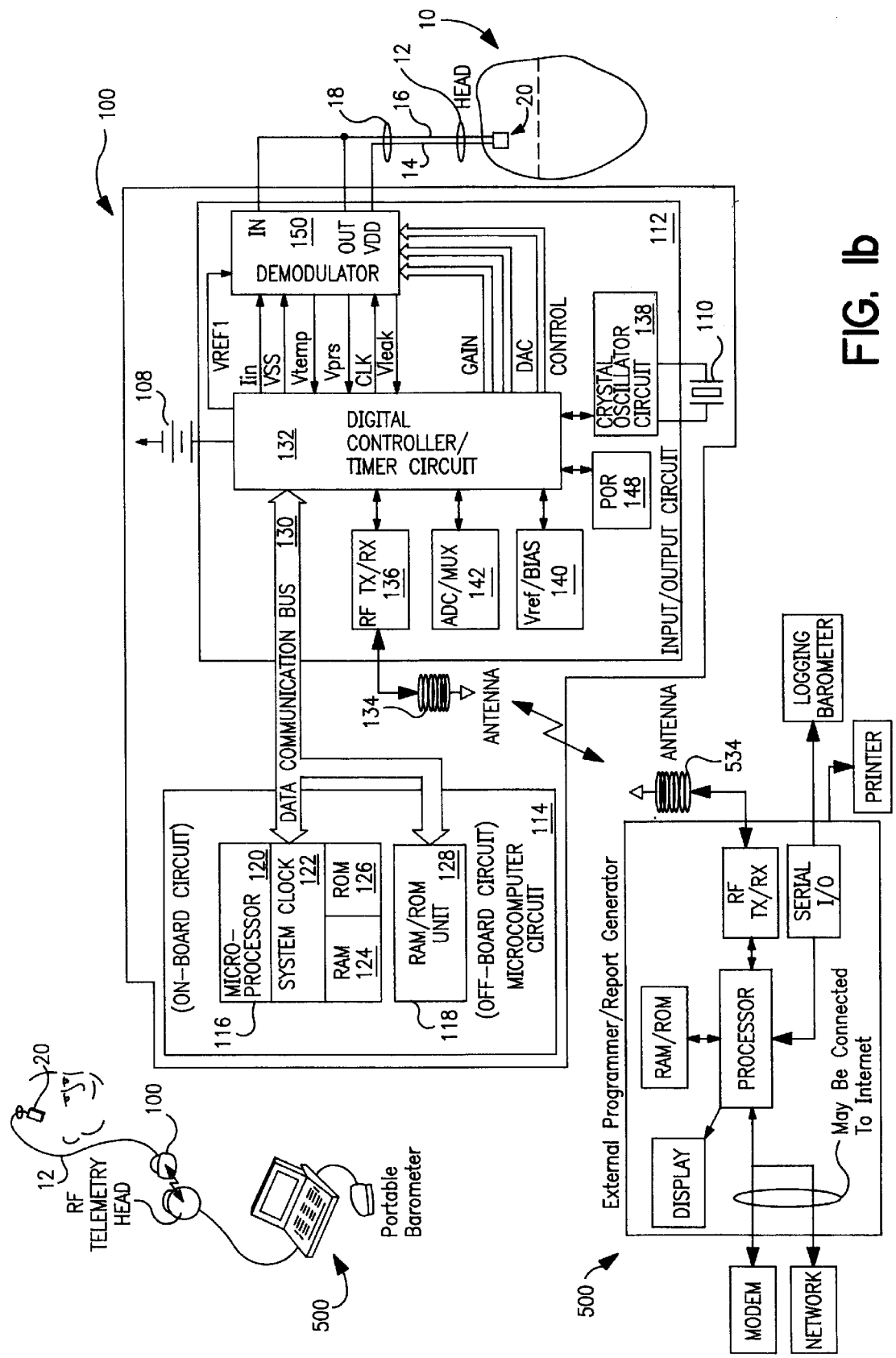
FIG. 1b is a block diagram of an implantable, programmable intracranial pressure/temperature data logger and lead system of the present invention.

FIG. 1a is a simplified block diagram of one embodiment of an intracranial physiologic signal monitoring system of the present invention comprising lead 12, IMD 100, and external device 500. The distal end of lead 12 containing sensor 20 is positioned in patient's head 10. In one embodiment of the present invention, lead 12 has first and second lead conductors 14 and 16 extending from a proximal connector end 18 to pressure sensor module 20 disposed near distal end 26 of lead 12. Pressure sensor module 20 most preferably includes a variable pickoff capacitor, a fixed reference capacitor, and signal modulating circuit described below in reference to FIGS. 4–12 which generates intracranial pressure and temperature time-modulated intervals. The proximal connector assembly of lead 12 is most preferably configured in a manner similar to that of a conventional, bipolar, in-line, pacing lead connector and is coupled to a connector block or connector (not shown in the Figures) of IMD 100. Such a connector block or connector is most preferably configured in a manner a similar to that of a conventional, bipolar, pacemaker pulse generator connector block assembly. The construction of lead 12 is described in more detail below in reference to FIGS. 2 and 3.

IMD 100, which in preferred embodiments of the present invention functions as a demodulator and transmitter, is divided generally into an input/output circuit 112 coupled to a battery 108, a telemetry antenna 134, the lead conductors 14, 16, a crystal 110, and a microcomputer circuit 114. The input/output circuit 112 includes the digital controller/timer circuit 132 and the associated components including the crystal oscillator 138, power-on-reset (POR) circuit 148, Vref/BIAS circuit 140, ADCIMUX circuit 142, RF transmitter/receiver circuit 136, and pressure signal demodulator 150.

Electrical components of IMD 100 and lead 12 shown in FIGS. 1a through 1d are powered by suitable implantable electrical energy source 108 in accordance with common practice in the art, and may be any one of a primary battery, a secondary battery, a capacitor, and so on. For the sake of clarity, the coupling of battery power to the various components of IMD 100 is not shown explicitly in the Figures. Antenna 134 is connected to input/output circuit 132 to permit uplink/downlink telemetry through RF transmitter and receiver telemetry unit 136. By way of example, telemetry unit 136 may correspond to that disclosed in U.S. Pat.

No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of various parameters. The specific embodiments of antenna 134, input/output circuit 132 and telemetry unit 136 presented herein are shown for illustrative purposes only, and are not intended to limit the scope of the present invention.

Crystal oscillator circuit 138 and crystal 110 provide the basic timing clock for the digital controller/timer circuit 132. Vref/BIAS circuit 140 generates stable voltage reference Vref and current levels from battery 108 for the circuits within the digital controller/timer circuit 132, and the other identified circuits including microcomputer circuit 114 and demodulator 150. Power-on-reset circuit 148 responds to initial connection of the circuitry to the battery 108 for defining an initial operating condition and also resets the operating condition in response to detection of a low battery voltage condition. Analog-to-digital converter (ADC) and multiplexer circuit 142 digitizes analog signals $V_{prs}$ and $V_{temp}$ received by digital controller/timer circuit 132 from demodulator 150 for telemetering by microcomputer circuit 114 via RF transmit/receive circuit 136 and antenna 134.

Data signals transmitted out through RF transmitter/receiver circuit 136 during telemetry are multiplexed by ADC/MUX circuit 142. Voltage reference and bias circuit 140, ADC/MUX circuit 142, POR circuit 148, and crystal oscillator circuit may correspond to any of those presently used in current implantable cardiac pacemakers.

The digital controller/timer circuit 132 includes a set of timers and associated logic circuits connected with the microcomputer circuit 114 through the data communications bus 130. Microcomputer circuit 114 contains an on-board chip including microprocessor 120, associated system clock 122, and on-board RAM and ROM chips 124 and 126, respectively. Microprocessor 120 may be interrupt driven to operate in a reduced power consumption mode normally, and be awakened in response to defined interrupt events, which may include the transfer of triggering and data signals on the bus 130 and the receipt of programming signals.

Microcomputer circuit 114 controls the operating functions of digital controller/timer 132, specifying which timing intervals are employed, and controlling the duration of the various timing intervals, via the bus 130. The specific current operating modes and interval values are programmable. The programmed-in parameter values and operating modes are received through the antenna 134, demodulated in the RF transmitter/receiver circuit 136 and stored in RAM 124.

Microprocessor 120 may be configured to operate as an interrupt driven device, so that is responsive to interrupts received from timing/control circuitry 132 corresponding to the occurrence of sensed signals meeting certain predetermined criteria such as intracranial pressure of a predetermined magnitude or temperature of a predetermined magnitude. Those interrupts are provided via data/address bus 130. Any necessary mathematical calculations to be performed by microprocessor 120 and any updating of the values or intervals controlled by timing/control circuitry 132 take place following such interrupts.

Data transmission to and from external device 500 may be accomplished by means of the telemetry antenna 134 and the associated RF transmitter and receiver 136, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. Uplink telemetry capabilities will typically include the ability to transmit real time intracranial pressure signals.

An active lead conductor 16 is attached through the connector block terminals to input and output terminals of demodulator 150 which supplies a voltage VREG at the output terminal. A passive lead conductor 14 is coupled through to the VDD supply terminal of the demodulator 150. The voltage signals $V_{prs}$ and $V_{temp}$ developed from intervals between current pulses received at the input terminal are provided by demodulator 150 to the digital controller/timer circuit 132. The voltage signals $V_{prs}$ and $V_{temp}$ are converted to binary data in an ADC/MUX circuit 142 and transmitted to the external display device via telemetry, where the $V_{prs}$ and $V_{temp}$ values are converted to pressure and temperature values through the use of calibration coefficients. These coefficients may be stored in the implanted system RAM or ROM, and be transferred by telemetry means to the external pressure display upon interrogation by the external display device, before $V_{prs}$ and $V_{temp}$ values are transmitted.

The voltage signal $V_{leak}$ developed from measurement of current through conductors 14 or 16 is converted to binary data by the ADC/mux circuit 142. This data correlates to the magnitude of leakage current through conductors 14 or 16 and through any external body fluid, matter or tissue. Normally this leakage would be very small since conductors 14 and 16 are insulated from the body. In the event a leakage path is created by a breakdown in the insulation of lead 12, however, $V_{leak}$ data are compared to a predetermined threshold and if the threshold exceeds the voltage VREG, the delivery of current to lead 12 is terminated to interrupt the leakage path. The leakage condition is then sampled at predetermined intervals, and in the event the sensed leakage current drops below a predetermined threshold level, VREG is restored to conductors 14 and 16 and operation of lead 12 is begun anew.

Intracranial pressure, temperature or other signals are sampled and digitized most preferably at a 256 Hz sampling frequency, and upon request from external device 500, may be telemetered to external device 500. In such a fashion a continuous stream of ICP data may be uplinked to external device 500. The amount of data transferred and the duration of the telemetry session may vary from a couple seconds to several minutes, or even extend over a period of days or weeks when data are uplinked to external device 500 at regular or intermittent predetermined intervals, depending on the intended use of the data. As shown below, a 256 Hz sampling frequency is about one-tenth the preferred operating frequency of sensor module 20 when pressure signals are being measured.

Intracranial temperature signals are most preferably digitized and stored once during each sampling interval. Such temperature data may be analyzed within IMD 100, by external device 500, by another device or may be interpreted by a physician to identify portions of the ICP cycle which are of interest, or to perform other diagnostic analyses of the transmitted or relayed data.

In general, the sampled intracranial pressure data telemetered externally by the implanted system represent absolute pressure values and do not account for changes in barometric pressure affecting the ambient pressure load on pressure sensor module 20. Physicians typically measure intracranial or body fluid pressure in relation to atmospheric pressure. Thus, in some embodiments of the present invention it is contemplated that barometric and absolute pressure are measured separately with separate measuring and recording equipment. Means for measuring and/or recording barometric pressure may be incorporated into external device 500, IMD 100, another device in communication with external device 500 and/or IMD 100, or a portion of lead 12 not located inside the skull.

FIG. 1b is a block diagram of one embodiment of an intracranial fluid pressure and temperature data logging system. In contrast to IMD 100 of FIG. 1a, IMD 100 of FIG. 1b now has onboard memory and processing capability to allow compression and storage of intracranial pressure, temperature or other signals from the lead 12, most preferably over a predetermined data storage interval of time. In one embodiment of the present invention, a number of power, timing and control signals described in greater detail below are applied by the digital controller/timer circuit 132 to demodulator 150 to initiate and power the operation of the pressure sensor module 20 and selectively read out the pressure and temperature signals $V_{prs}$ and $V_{temp}$.

Figure 1C:
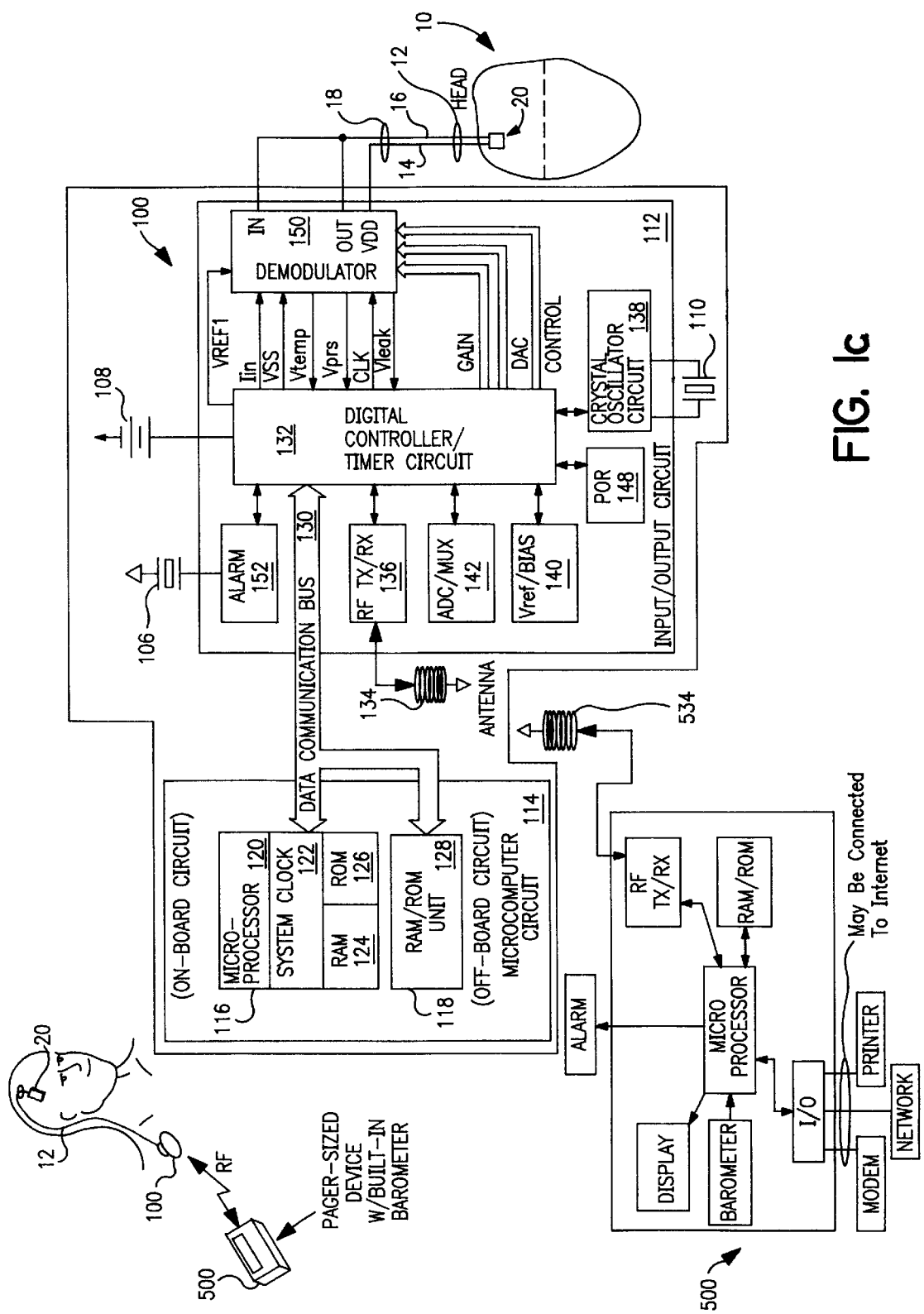
FIG. 1c is a block diagram of an implantable, programmable intracranial pressure/temperature monitor and lead system of the present invention.

FIG. 1c is a block diagram of an intracranial pressure and temperature monitoring system, which differs from the data logger of FIG. 1b in that the physician or healthcare specialist may program predetermined criteria, thresholds, limits or levels for selected parameters of interest into IMD 100 and/or external device 500. When those predetermined criteria, thresholds, limits or levels are met, exceeded or dropped below, an alarm or alert may be triggered or provided such that the patient or a healthcare attendant is made aware of a detected change in the patient's intracranial state or condition. The alarm can be as simple as a piezo-electric buzzer crystal attached to the inside surface of IMD 10 which is activated upon receiving an appropriate command from external device 500 or IMD 100.

Since access to atmospheric or barometric pressure information is generally required to accurately assess ICP levels, a method for combining such data with ICP data is desirable, and may be facilitated by transferring data acquired by an external barometer to IMD 100 by, for example, RF telemetry, where the data are combined to yield gage pressure. Alternatively, ICP data from IMD 100 may be transmitted by RF telemetric or other means to an external device containing the barometer (such as external device 500), where ICP data representing absolute intracranial fluid pressure data are combined with atmospheric pressure to yield gage pressure, which is then most preferably compared to predetermined or pre-programmed criteria, thresholds, limits or levels to determine whether a problem exists. The latter configuration lends itself more readily to sophisticated monitoring, analysis, alarm and therapy delivery embodiments of the present invention, as the hardware and capabilities of IMD 100 can be focused on the accurate measurement of physiologic intracranial signals, long life and the like.

IMD 100, lead 12 and external device 500 can be configured into a system capable of issuing an alert or alarm to the patient or a healthcare professional when a predetermined condition or state of the intracranial environment is detected or sensed through the generation or control of visual warnings or advisories, transmission of alarms and information to a healthcare worker from a remote patient site via telephone, hardwire, cell phone, satellite or the internet, or by transmission through a hospital monitoring network.

External device 500 may be a bedside module with a built-in barometer and telemetry means to communicate with IMD 100 via a patch antenna or telemetry head configured for bedridden patients, or may alternatively be a small wearable device akin to a pager, pendant or watch having a built-in barometer and telemetry means. In some embodiments of external device 500 of the present invention, the patient may even be ambulatory.

Figure 1D:
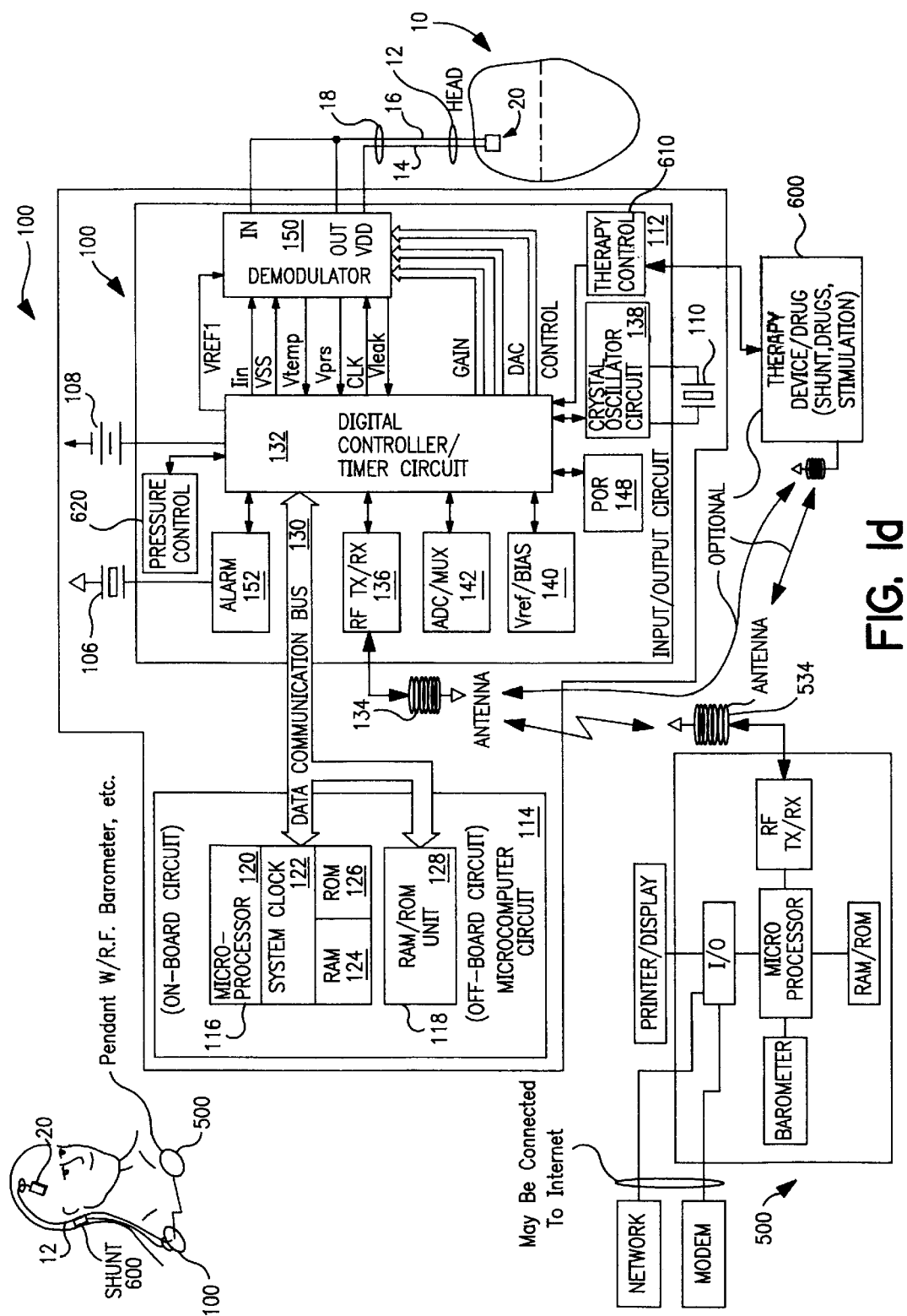
FIG. 1d is a block diagram of an implantable, programmable intracranial pressure/temperature controller and lead system of the present invention.

FIG. 1d is a block diagram showing one embodiment of an intracranial pressure, temperature or other intracranial physiologic signal monitoring system which is further employed to control the delivery of a therapy to the patient. The therapy delivered may be the delivery of a drug, the opening or closing or of a shunt or valve, the provision of electrical stimuli, and the like. In the manner described in respect of FIG. 1c above, intracranial data are compared within IMD 100 or external device 500 to predetermined criteria, thresholds, limits or values set by the physician or healthcare worker, and if exceeded, action is taken by triggering a therapy designed to keep the selected parameter of interest within limits.

Figure 14:
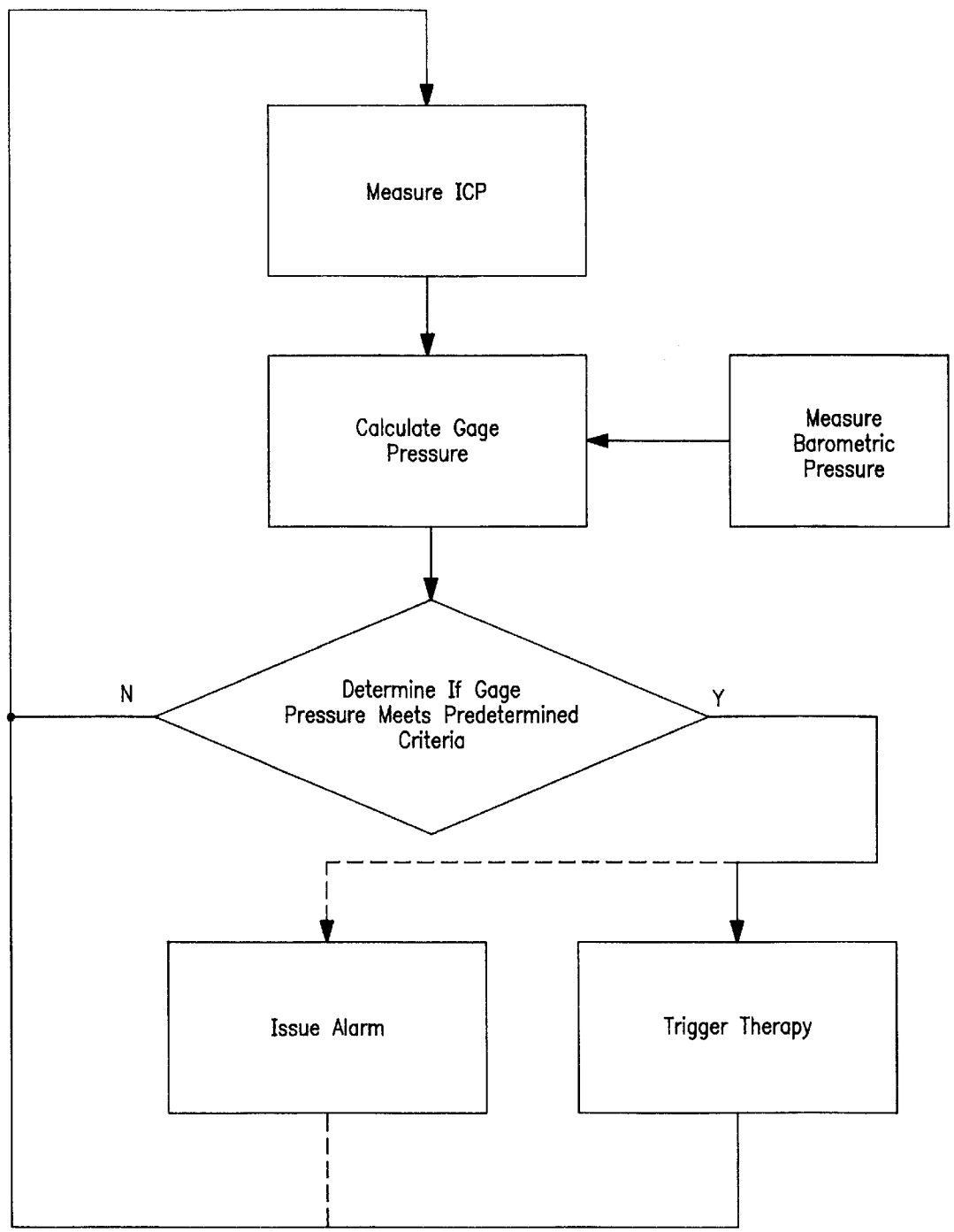
FIG. 14 shows a flow chart for some embodiments of methods of the present invention.

In one such embodiment of the present invention, ICP data are used by IMD 100 or external device 500 to control the opening or closing of a shunt or valve which drains off or stops the draining of cerebral spinal fluid. As in the monitoring system of FIG. 1c, it is generally important to correlate absolute intracranial pressure with atmospheric pressure to derive an accurate representation of intracranial fluid pressure. This may involve sending by telemetric means a barometer reading from an external device to IMD 100. Alternatively, and as described above in connection with a monitoring embodiment of the present invention, absolute intracranial pressure data may be transmitted via telemetric or other means to external device 500, where combination of barometric pressure and ICP data occurs to derive intracranial gauge pressure or to control the delivery of a therapy. FIG. 14 illustrates the general steps of the present invention as they apply to the operation of IMD 100, lead 12 and external device 500, and as they relate to the operation of the systems shown in FIGS. 1a through 1d. Note that the various components and sub-components disclosed in FIGS. 1a through 1d may be mixed and matched in a virtually infinite number of permutations and combinations falling within the scope of the present invention.

Pressure Sensor and Lead Construction

Referring now to FIGS. 2 through 13, there is shown a preferred embodiment of an intracranial pressure sensor of the present invention. Pressure sensor capsule or module 20 located most preferably at the distal end of lead 12 is most preferably constructed with a titanium outer housing having an integral, pressure deformable, planar sensing membrane or diaphragm disposed therewithin, the plate or diaphragm forming one plate of a variable or pickoff capacitor $C_P$. The other plate of the pickoff capacitor $C_P$ is fixed to one side of a hybrid circuit substrate 151 hermetically sealed within the outer housing.

The capacitance of pickoff capacitor $C_P$ varies as the diaphragm is deformed by pressure variation patient's cranial cavity 10 or elsewhere in the neurological system. A reference capacitor $C_R$ is also formed with fixed spacing between planar capacitor plates formed on the same side of the hybrid circuit substrate and on the outer housing to provide a reference capacitance value.

Pressure (and temperature) sensor circuitry most preferably disposed within module 20 employs voltages VDD and VREG supplied by IMD 100 and demodulator 150 to alternately charge and discharge the capacitor pair with charge and discharge currents that vary in a predetermined manner as a function of temperature, and provide instantaneous absolute pressure and temperature modulated charge time intervals to demodulator 150 in a manner that will be described below.

Figure 2:
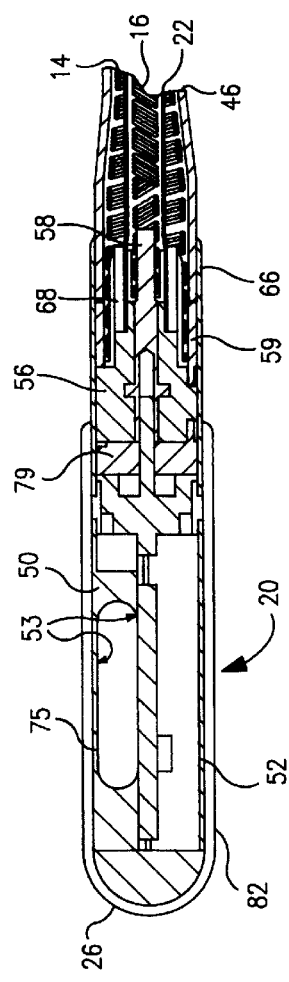
FIG. 2 is a cross-section assembly view of the distal end of a pressure sensing lead that may be employed in the systems of FIG. 1.
Figure 3:
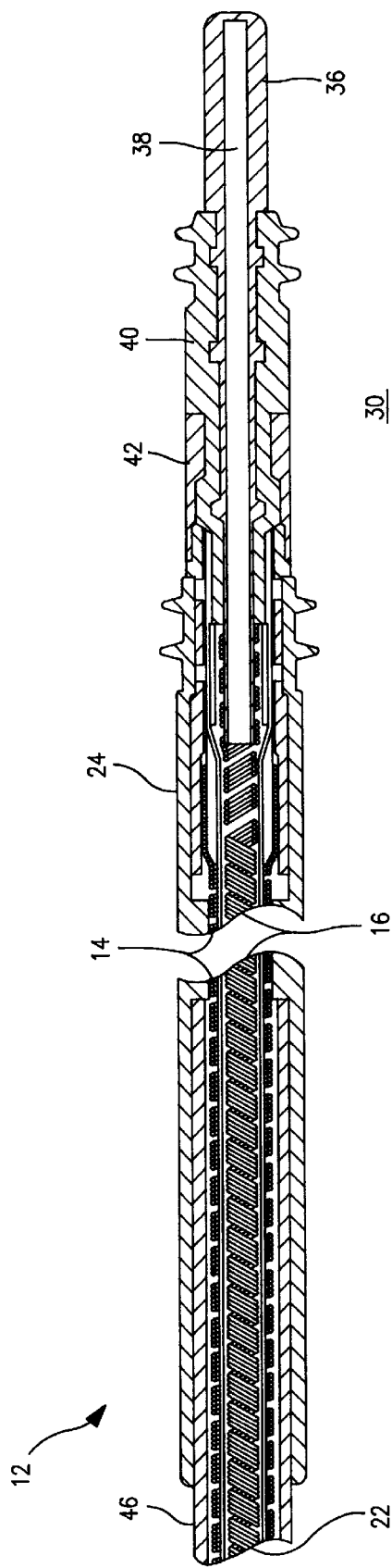
FIG. 3 is a cross-section assembly view of the proximal end of a pressure sensing lead that may be employed in the systems of FIG. 1.

FIGS. 2 and 3 are respective cross-sectional views of the distal and proximal end sections of lead 12 of FIGS. 1a through 1d. Pressure sensor module is located just proximal to distal tip 26 and is mechanically and electrically connected to the coaxial, outer and inner, coiled wire lead conductors 14 and 16.

The passive and active coiled wire lead conductors 14 and 16 are separated by an inner insulating sleeve 22 and encased by an outer insulating sleeve 46 extending between in-line connector assembly 30 and pressure sensor module 20. A stylet receiving lumen is most preferably formed within inner coiled wire lead conductor 16 and extends to the connection with sensor module 20.

In-line connector assembly 30 includes an inner connector pin 36 having a stylet receiving, pin lumen 38 and is attached to the proximal end of the inner coiled wire conductor 16 to align the pin lumen 38 with the stylet receiving lumen of the inner coiled wire conductor 16. An insulating sleeve 40 extends distally over the inner connector pin 36 and separates it from a connector ring 42. Connector ring 42 is electrically and mechanically attached to the proximal end of the outer coiled wire conductor 14. An exterior insulating connector sleeve 24 extends distally from the connector ring 42 and over the proximal end of the outer sleeve 46.

The distal ends of the outer and inner coiled wire conductors 14 and 16 are attached to the proximal end of the pressure sensor module 20 to provide the VDD and the input/output connections to the on-board pressure sensor hybrid circuit described below.

The materials used to form the foregoing lead components and the construction and attachments depicted in FIGS. 2 and 3 are well known in the art of bipolar coaxial pacing leads and deep brain leads having in-line connectors.

Such lead technology is employed, for example, in the fabrication of the Medtronice bipolar pacing lead Model 4004M. The specific materials, design and construction details are not important to the understanding and practice of the present invention.

Figure 4:
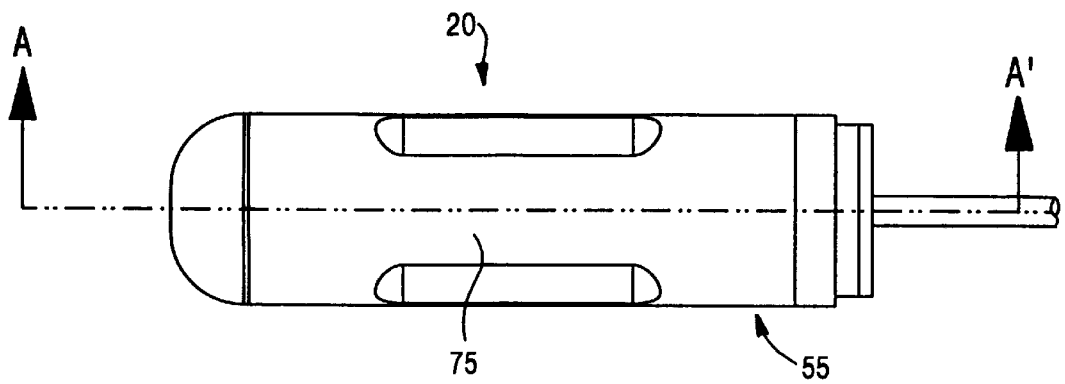
FIG. 4 is a top subassembly drawing of the pressure sensing module incorporated into the distal end of the pressure sensing lead of FIG. 2.
Figure 5:
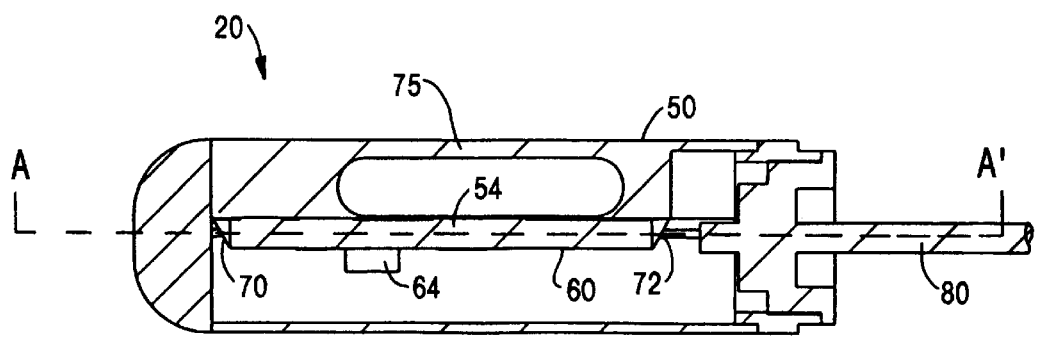
FIG. 5 is a side cross-section view of the internal components of the pressure sensing module taken along line A—A of FIG. 4.
Figure 6:
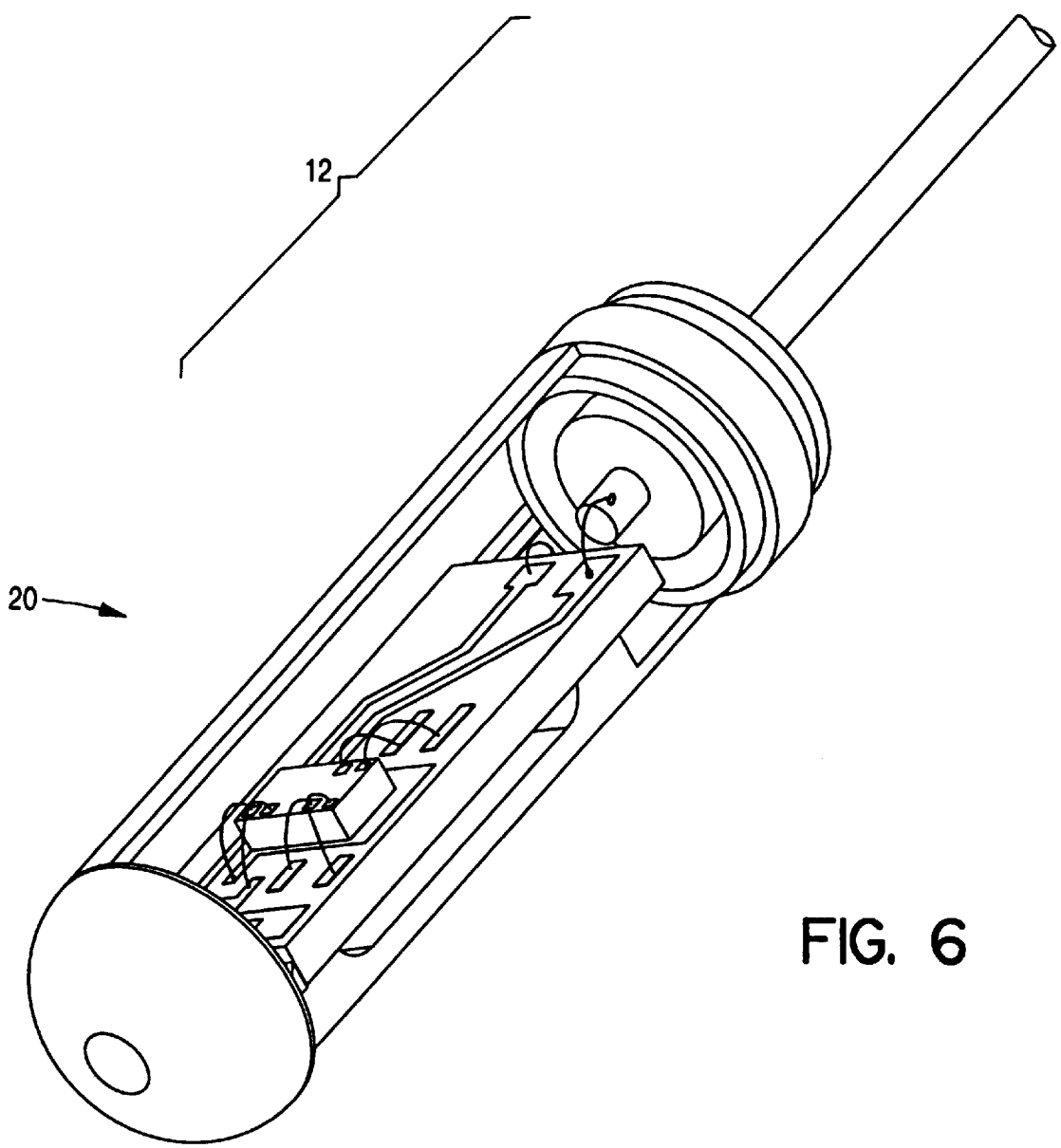
FIG. 6 is a partial cutaway perspective view of the attachment of the pressure and temperature signal modulating circuit to the feedthrough and housing of the pressure sensing module.
Figure 7:
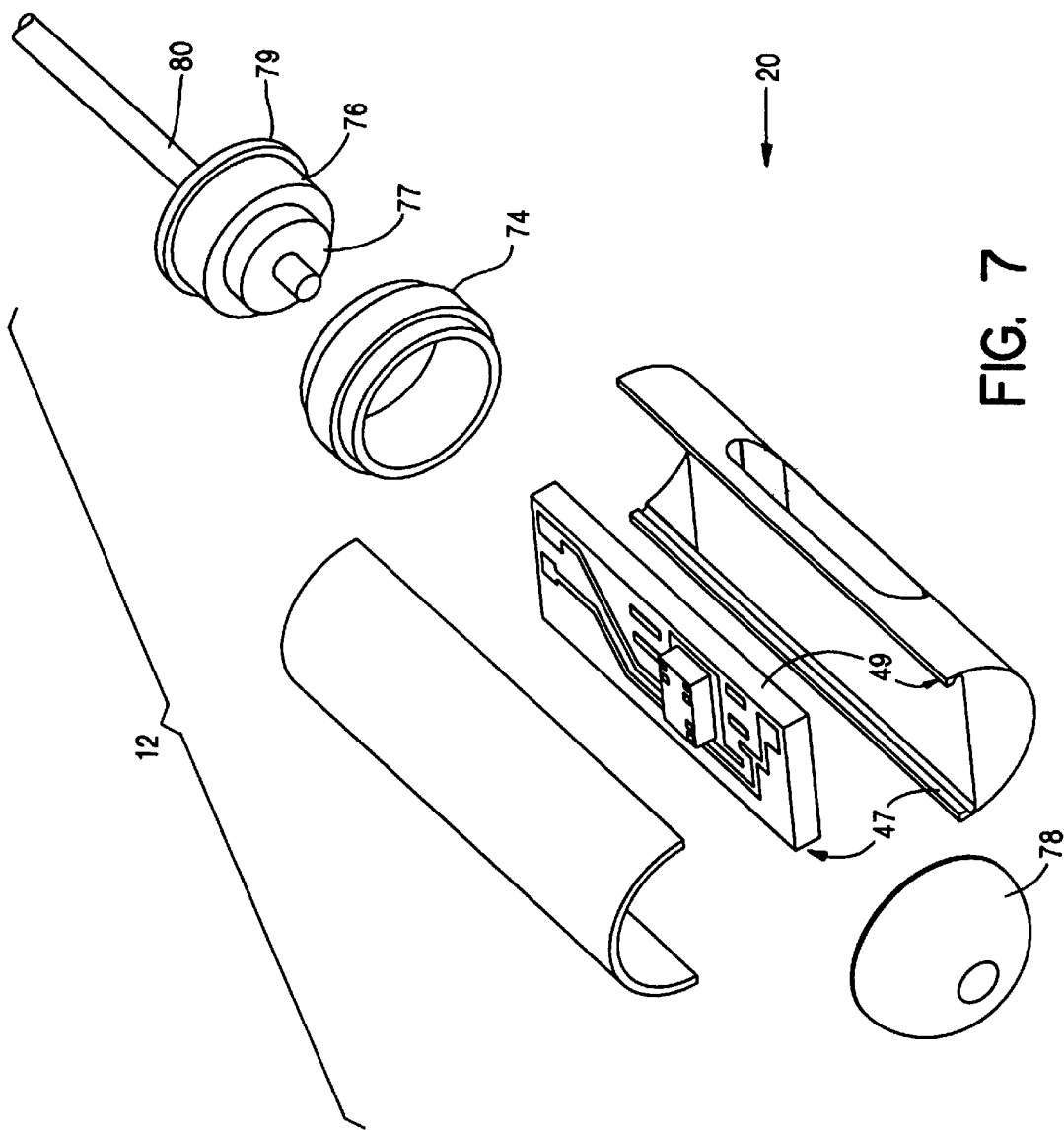
FIG. 7 is an exploded perspective view of the components of the pressure sensing module.
Figure 8:
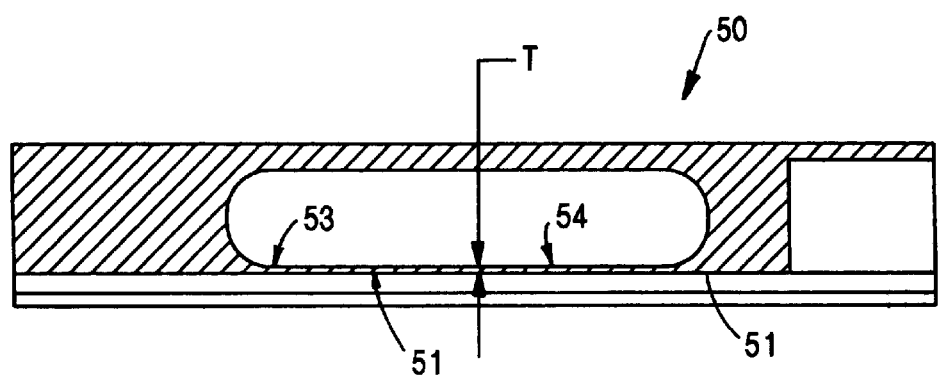
FIG. 8 is a side cross section view of a housing member and diaphragm of FIG. 7.

Turning now to the construction of pressure sensing capsule or module 20, reference is first made to the assembly drawings, including the enlarged top and side cross-section views of FIGS. 4 and 5, the partial section view of FIG. 6 and the exploded view of FIG. 7. The pressure sensing module 20 is most preferably formed with first and second titanium outer housing half members 50 and 52, which when joined together as assembled titanium housing 55, surround a ceramic hybrid circuit substrate 60 supporting the sensing and reference capacitors and pressure signal modulating circuitry. The pressure signal modulating circuit (described in detail below with reference to FIGS. 10 and 11) preferably includes IC chip 64 mounted to one surface of the substrate 60 and attached to electrical terminal pads and board feedthroughs to the other surface thereof. Substrate 60 is supported in a manner described below in a fixed relation with respect to housing member 52 by the proximal and distal silicone adhesive fillets 70 and 72 and parallel side walls 47 and 49 (shown in FIG. 7). Feedthrough 76 includes ceramic insulator 77 located between feedthrough ferrule 79 and feedthrough wire 80 to electrically isolate feedthrough wire 80, which in turn is electrically connected to a pad on substrate 60.

Diaphragm structure 50 most preferably includes a tissue shielding member 75 which spans between the proximal and distal ends of the diaphragm, and is elevated above the external surface of the pressure sensing diaphragm. The purposes of such a structure are to protect the diaphragm from coming into contact with anatomical structure or tissue which might cause erroneous pressure readings, to add stiffness to the sensor assembly, and to protect the thin diaphragm from damage during handling. Shielding member 75 is optional, and may be omitted if desired.

Internal electrical connections between sensor IC chip 64 and the substrate are most preferably established by aluminum wire-bonds as shown in FIG. 6. Connection between the hybrid traces and both the feedthrough pin 80 and the sensor titanium case 50 are also made via gold wire-bonds. Conventional wire-bonding is used with each trace, while the connections to the feedthrough pin 80 and case 50 are made using conductive silver epoxy. The specific electrical connections are described below in conjunction with the electrical schematic diagram of the sensor module electronic circuit in FIG. 11.

After the mechanical and electrical components of the pressure sensing module 20 are assembled together, the titanium housing half members 50 and 52 and the nose element and adapter ring 74 are laser welded together as hermetically sealed, assembled titanium housing 55. Then, the module 20 is attached to the components of the lead 12 to provide the electrical and mechanical connections with the outer and inner, passive and active, coiled wire lead conductors 14 and 16 as described below.

As shown in FIG. 2, module 20 is electrically and mechanically attached to the outer and inner coiled wire conductors 14 and 16 at the proximal end thereof through an intermediate transition assembly similar to a feedthrough and including an insulating body 56 separating an inner, conductive transition pin 58 from distal and proximal outer conductive transition sleeves 57 and 59. Sleeves 57 and 59 are laser welded together for electrical and mechanical connection.

The distal transition sleeve 57 is welded to the ferrule 79 and the distal end of the transition pin 58 is staked to the feedthrough pin 80. The distal end of the inner transition pin 58 is hollow and extends out of the insulating body 56 to receive the proximal end of the feedthrough pin 80. Staking is accomplished through access ports in the molded insulating body 56, and then the access ports are filled with silicone adhesive. In this fashion, the inner transition pin 58 is electrically coupled to the feedthrough pin 80, and the outer transition sleeves 57 and 59 are electrically connected to the assembled titanium housing 55.

The proximal end of the inner transition pin 58 is slipped into the distal lumen of the inner coiled wire conductor 16. The distal end of the inner coiled wire conductor 16 is crimped to the proximal end of the inner transition pin 58 by force applied to a crimp sleeve 66 slipped over the distal segment of the coiled wire conductor 16. The distal end of inner insulating sleeve 22 is extended over the crimp sleeve 66 and adhered to the insulating body 56 to insulate the entire inner conductive pathway. The outer coiled wire conductor 14 is attached electrically and mechanically by crimping it between the outer transition sleeve 59 and an inner crimp core sleeve 68 slipped between the distal lumen of the outer coiled wire conductor 14 and the inner insulating sleeve 22. Silicone adhesive may also be used during this assembly. When the electrical and mechanical connections are made, the active coiled wire conductor 16 is electrically connected to a pad or trace of the substrate 60, and the passive coiled wire conductor 14 is electrically attached through the housing half members 50 and 52 to a further substrate pad or trace as described below.

The distal end of the pressure sensing module 20 is attached to the distal lead assembly including further outer sleeve 34 and coiled wire conductor 32 described above. At the distal end of the pressure sensing module 20, a crimp pin 81 is inserted into the lumen of the further coiled wire conductor. The crimp pin 81 and the further coiled wire conductor 32 are inserted into the tubular nose element 78 which is then crimped to the coiled wire conductor 32 and crimp pin 81. The further outer sleeve 34 extends over the crimp region and the length of the further coiled wire conductor 32. The distal end of the further coiled wire conductor 32 is attached by a similar crimp to the inner tip core member 28 using a further crimp pin 27.

Figure 9:
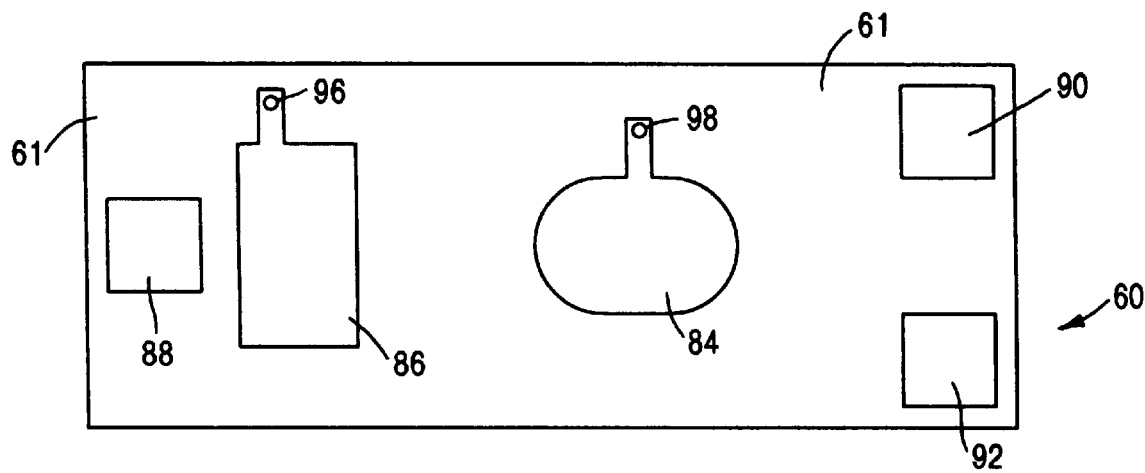
FIG. 9 is a bottom view of the IC hybrid circuit substrate of FIG. 7.

Returning now to FIGS. 4 and 5, and 8, thin titanium diaphragm 54 is machined into the titanium outer housing half member 50. The flat inner surface of diaphragm 54 in combination with a peripheral continuation of that surface form plates of a pair of planar capacitors, the other plates of which are deposited onto the adjacent surface 61 of the ceramic hybrid substrate 60 as shown in FIG. 9. An external pressure change results in displacement of the diaphragm 54 and subsequent change in capacitance between the diaphragm 54 and one of the deposited substrate plates. This change in capacitance of the pickoff capacitor $C_P$ with change in pressure is approximately linear over the pressure range of interest, and is used as a measure of the pressure outside the sensor module 20. The external pressure change has no effect on the second, reference capacitor $C_R$.

To electrically isolate diaphragm 54 from the patient's body, materials must be employed that do not absorb significant amounts of body fluids and thus swell (which in turn would otherwise cause the deflection of diaphragm 54 and changes the capacitance of the pickoff capacitor $C_P$). The materials employed be must also be uniformly thin and repeatably manufacturable so as to avoid affecting the sensitivity of the pickoff capacitor $C_P$. Finally, the materials employed must adhere well to diaphragm 54 so that bubbles, gaps or other separations do not occur over time. Such separations might otherwise cause drift in the sensed capacitance.

Returning now to FIG. 2, the outer sleeve 46 and further sleeve 34 are formed of conventional urethane tubes employed in fabricating pacing leads. For adherence to outer sleeve 46 and further sleeve 34, a thin urethane sensor jacket or covering 82 is employed that extends over the full length of the sensor module 20 and is adhered at its ends to the outer insulating sleeve 46 and the further outer insulating sleeve 34, e.g. as by urethane based adhesives. The urethane covering 82 is employed to cover the majority of the sensor module 20 but the material does not always adhere well to the metal surfaces thereof, even when a primer is employed. The loss of adherence over the diaphragm 54 can lead to accumulation of fluids and affect the response time to changes in intracranial or body fluid pressure. Therefore, it is preferable to substitute a well-adhering, body compatible, insulating coating over the diaphragm 54.

Such a coating may be formed as follows: A cut-out portion of the sensor covering 82 is made following the periphery 53 in order to expose the diaphragm or diaphragm 54. A thin, uniform thickness coating 45 of silicone adhesive is applied over the exposed diaphragm 54 and other areas within the cavity formed by the diaphragm and bar 75 that adheres thereto without any fluid swelling or separation occurring over time. The silicone adhesive does not adhere well to the edges of the cut-out section of the urethane covering 82, but may be injected between the edges and the half member 50 to fill up any remaining edge gap.

The resulting composite covering 82 and insulating layer electrically insulates the titanium outer housing half members 50 and 52 that are electrically connected to VDD. The combined housing is formed by welding the half members 50 and 52 together and to the adapter ring 74 and nose element 78. When assembled, the sensor capsule or module 20 is preferably about 0.110 inches in diameter, including the polyurethane insulation covering 82, and is approximately 0.49 inches long.

Alternatively, the polyurethane material used to construct the lead insulation tubing 22 and 46 may be replaced by a silicone material. In this configuration, the sensor covering could be silicone tubing with silicone adhesive disposed on the diaphragm structure as in the previously described embodiment, or the capsule could be dipped, sprayed, sputtered, or the like to cover the entire capsule surface, including the diaphragm, with silicone material.

A further refinement of the lead body is to pre-form a right-angle bend in the lead body just proximal of the sensor assembly. This embodiment of the present invention is particularly suitable for measuring intracranial pressure in the subarachnoid space, but preforming the bend. A right-angle transition section in the lead body or other bend may also be employed to reduce the stress exerted on the lead body as a result of the lead body having to be bent to lay against the skull after exiting the burr hole.

The cylindrical housing half members 50 and 52 are machined in the two pieces using wire electric discharge machining (EDM) methods. In the first housing half member 50, the thin diaphragm 54 is approximately 0.0013 inches thick ("T" in FIG. 8) and is produced through precision EDM of the interior and exterior surfaces of the titanium stock. The inner surface 51 of the half member 50 extends as a continuous planar surface beyond the perimeter 53 of the diaphragm 54 to provide one plate of the reference capacitor $C_R$ in that region.

Turning now to FIG. 9, the ceramic sensor hybrid circuit substrate 60 consists of a 90% alumina board, on the back side 61 of which are deposited an oval capacitor plate 84 coupled to a plated substrate feedthrough 98, a second capacitor plate 86 coupled to a plated substrate feedthrough 96, and three plated standoffs 88, 90, 92. The oval capacitor plate 84 is dimensioned to generally conform to the shape of the diaphragm 54 under deflection and fall within the perimeter 53. The adjacent rectangular capacitor plate 86 is dimensioned to fall outside the perimeter 53. The inner surface 51 of half member 50 provides a reference surface for locating the capacitor plates 84 and 86 relative to the diaphragm 54.

When assembled, the plates 84 and 86 are spaced from the inner surface 51 of the housing half member 50 by the difference in thicknesses of the standoffs 88–92 and the plates 84 and 86 to form the pickoff capacitor $C_P$ and reference capacitor $C_R$. The pressure sensing pickoff capacitor $C_P$ employing central capacitor plate 84 varies in capacitance with pressure induced displacement of the diaphragm 54 and the silicone adhesive layer applied thereto. The reference capacitor $C_R$, employing the adjacent reference capacitor plate 86 located in the region where diaphragm 54 deflection is zero within the operating pressure range, varies in capacitance with common mode changes in sensor voltages, thermal expansion effects, and changes in the hermetically sealed capacitor dielectric constant.

The two capacitor plates 84 and 86 are electrically connected to the front side of the substrate 60, on which the sensor electronic circuit included in the IC chip 64 is mounted. The common capacitor plate surface 51 is coupled to VSS. The sensor electronic circuit alternately charges and discharges the pickoff and reference capacitors $C_P$ and $C_R$ through a constant current source which varies with temperature change inside the sensor module 20. The temperature-related changes in the charging current affects the charge times for both the pickoff and reference capacitors $C_P$ and $C_R$ equally. However, temperature induced changes in internal pressure within the sensor module 20 (and external pressure changes) only affect the pickoff capacitor $C_P$ plate spacing, which causes an increase or decrease in the capacitance and subsequent increase or decrease in the time to charge the pickoff capacitor $C_P$ to a set voltage level.

An additional desirable feature of hybrid 60 is to provide a set of bootstrap shield platings at the midplane of substrate 60 that cover the same footprint as capacitor plates 84 and 86. The purpose of such platings is to reduce parasitic capacitance between the plates 84 and 86 and the conductors on the top surface of the substrate 60. The bootstrap circuit works by imposing a voltage on the bootstrap plating equal to the voltage on the corresponding capacitor plate 84 or 86. Since capacitance exists only in relation to a difference in voltage, the capacitance between the capacitor plates 84 and 86 and the bootstrap platings is zero by definition, and thus the bootstrap plating provides 100% shielding between the plates 84 and 86 and the top surface of the substrate 60.

Intracranial pressure changes cause an increase or decrease of the pickoff capacitor $C_P$ plate spacing, which causes a decrease or increase, respectively, in the capacitance and subsequent decrease or increase, respectively, in the time to charge the pickoff capacitor $C_P$ to a set voltage level, assuming an unchanged intracranial temperature and constant charging current. Since no gap change between common plate surface 51 and the adjacent capacitor plate 86 due to pressure change occurs at the reference capacitor $C_R$, there is no pressure induced reference capacitance change. The ratio of the charging time of the pickoff capacitor $C_P$ to the sum charging time of the reference and pickoff capacitors $C_R$ and $C_P$ provides a stable indication of pressure induced changes and cancels out common mode capacitance changes, resulting in an absolute pressure signal. The common mode capacitance change, principally temperature related, can be derived from the capacitance of the reference capacitor $C_R$.

The substrate surface 61 platings shown in FIG. 9 are specially designed to provide precise control of the pickoff and reference capacitor gaps without the need for an excessive number of close-tolerance components. By specifying a single tight tolerance between the top surfaces of the standoff platings and the top surfaces of the capacitor platings, the spacing between the reference and pickoff capacitor plates and the planar surface 51 of the sensor diaphragm 54 can be very accurately controlled. Because the inner surface 51 of the diaphragm 54 extends beyond the perimeter 53 of the diaphragm 54 to the region where the standoffs 88–92 make contact, the difference between the height of the standoff pads and the height of the capacitor plates 84 and 86 will define the gap between the capacitor plates 84, 86 and the inner surface 51.

The hybrid standoffs 88–92 are pressed into contact against the inner surface 51 by the shrinkage of the silicone adhesive fillets 70, 72 when the components are assembled and the silicone adhesive cures, with the shrinkage increased by curing at an elevated temperature. The assembly creates a net residual tensile force in the silicone fillets and resultant interference fit exerting pressure between the surface 51 and the standoffs 88–92. Lateral constraint of the substrate 60 is provided by the fit of the hybrid circuit substrate 60 in the housing half member 50 between the lateral side walls 47 and 49 in one axis, and by the silicone adhesive 70, 72 along the other axis. The result is an accurate and permanent location of the substrate 60 within the cavity of the sensor module 20 with no residual stress in the critical metal and ceramic parts which might cause drift of the sensor signal over time.

This approach to spacing the pickoff and reference capacitor $C_P$ and $C_R$ plates has two major advantages. First, only one set of features, that is the plating heights or thicknesses, need to be in close tolerance, and those features are produced through a process which is extremely accurate. For, example, the standoffs 88, 90, 92 can be precisely plated to a thickness of 0.0011, and the capacitor plates 84, 86 can be plated to 0.005 inches. A gap of 0.0006 inches with a tolerance of 0.0001 inches can thereby be attained between the capacitor plates 84, 86 and the diaphragm inner surface 51. The second advantage is the near absence of signal modulation by thermal expansion effects. Thermal change in dimension of the structure which establishes the gap between the plates 84, 86 and the sensor diaphragm inner surface 51 is per the relation D I=a DT I, where D I is the change in gap, a is the thermal expansion coefficient of the material creating the gap, DT is the variation in temperature, and I the length of the structure.

In the example provided, the gaps are only 0.0006" thick, so change in gap over an expected variation in temperature in vivo of 1° C., assuming coefficient of thermal expansion for the standoff material of around $13\times10^{-6}/°$ C., would result in a gap change of 7.8 nano-inches. This thermal change is about sixty times less than the gap change for 1 mm Hg pressure change, and much less than can be detected using state of the art low-current methods.

There is one significant thermal effect. When the pressure sensor module 20 is sealed using a laser welding process, a volume of gas (mostly Helium and Nitrogen) at or near atmospheric temperature and pressure is trapped inside the cavity of the sensor module 20. The difference between the gas pressure inside the cavity and the outside pressure influences the gap of the pickoff capacitor $C_P$. At the instant the sensor is sealed, there is zero pressure differential and consequently no deflection of the pressure diaphragm 54 from its neutral position. But the gas inside the sensor must comply with the classical gas law PV=nRT. Assuming then that the volume inside the sensor is constant, and that the mass quantity and gas constant (n and R, respectively) are constant (since no gas enters or leaves the sensor cavity after sealing), the effect of temperature change can be described by the gas law formula as $P_2=P_1(T_2/T_1)$.

In the human body, the temperature may vary from the nominal 37° C. (±2° C.). The variation may be between ±3° C. with fever and between −1° C. to +2° C. with exercise. Assuming that the sensor were sealed at 300K and 760 mm Hg, the gas law formula implies that for every 1° C. change in temperature there is a corresponding change of over 2 mm Hg in internal pressure. This will manifest itself as a decrease in the pressure value reported by the sensor with increasing temperature, since the cavity pressure against which external pressure is compared has increased. This is a significant error and needs to be compensated for. In accordance with a further aspect of the present invention, the charging time of the reference capacitor $C_R$, which will vary as a function of temperature due to variation of band-gap regulator current of approximately 1%/° C., is monitored. The change in charging time Ttemp of the reference capacitor $C_R$ is stored in the monitor 100, and used to correct for changing temperature effects.

As previously mentioned, the feature which physically responds to pressure to produce a change in pickoff capacitance is the thin diaphragm 54 in housing half member 50 created via a wire EDM process. The deflection y measured at the center of the diaphragm 54 is governed by the equation:

$$y_{max} = k_1(wr^4/Et^3)$$

where w is the pressure applied to one side of the diaphragm 54 (or the pressure difference), r is the width of the rectangular diaphragm 54, E is Young's Modulus for the diaphragm material, t is the thickness of the diaphragm, and $k_1$ is a constant determined by the length-to-width ratio of the diaphragm 54. In the present invention, a ratio of 1.5:1 was used for the sensor diaphragm 54 dimensions, yielding $k_1$=0.024, which has been found to be optimal ratio in trading off sensor length vs. signal strength, i.e., a lengthening the diaphragm beyond current ratio yields progressively less additional signal for the additional length. In a specific construction employing the 1.5:1 ratio and a diaphragm thickness T of 0.0013 inches, and a gap of 0.0005 inches, a baseline capacitance of approximately 1.5 pF was realized for both the pickoff and reference capacitors, $C_P$ and $C_R$ counting a capacitance contribution of the sensor IC chip 64. Baseline capacitance is preferably large in comparison to expected parasitic capacitances, especially those which would tend to vary over time or in response to environments, but not so large as to demand overly large charging currents. Also, the capacitances are preferably large enough to keep the oscillation frequency of the pickoff circuit around 4–6 kHz without resorting to extremely low charging currents, which would tend to decrease signal-to-noise ratio. Preliminary prediction for change in capacitance in response to pressure change is 0.5–1.5 fF/mm Hg.

The preferred embodiment of the reference and pickoff capacitors described above and depicted in the drawings, positions the reference capacitor plate 86 in a ring shape surrounding the pickoff capacitor plate 84 on substrate surface 61. It will be understood that the reference capacitor plate 86 may have a different shape and be positioned elsewhere on the substrate surface 61. For example, both the reference capacitor plate 86 and the pickoff capacitor plate 84 may be square or rectangular and positioned side by side on the substrate surface 61. Regardless of the configuration or position, the reference capacitor plate would be located outside the perimeter 53 of the diaphragm 54 and spaced away from the inner surface of the diaphragm 54 in the same fashion as described above. Moreover, in any such configuration, the diaphragm 54 and the pickoff capacitor plate 84 may also have a different shape, e.g. a more square shape than shown.

Pressure and Temperature Signal Modulating Circuit

Figure 10:
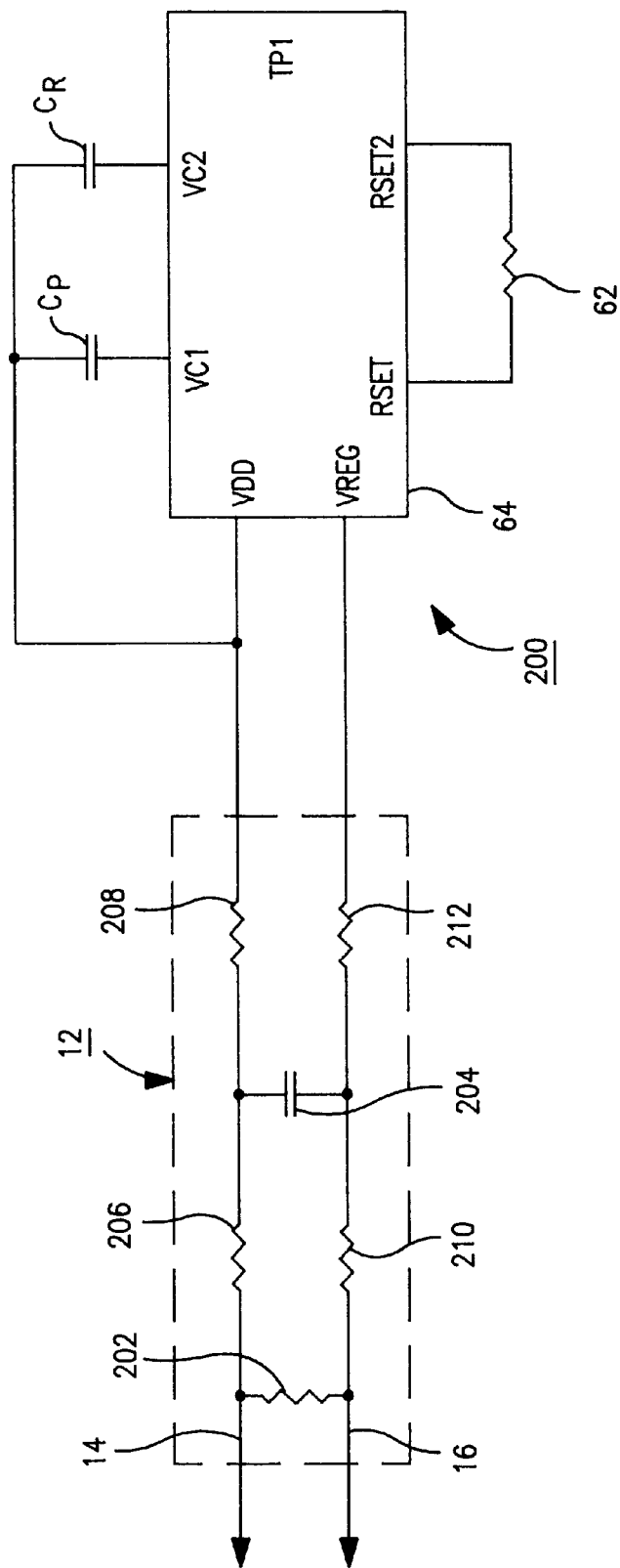
FIG. 10 is a schematic diagram of the pressure sensing lead impedance network and the pressure and temperature signal modulating circuit.
Figure 11:
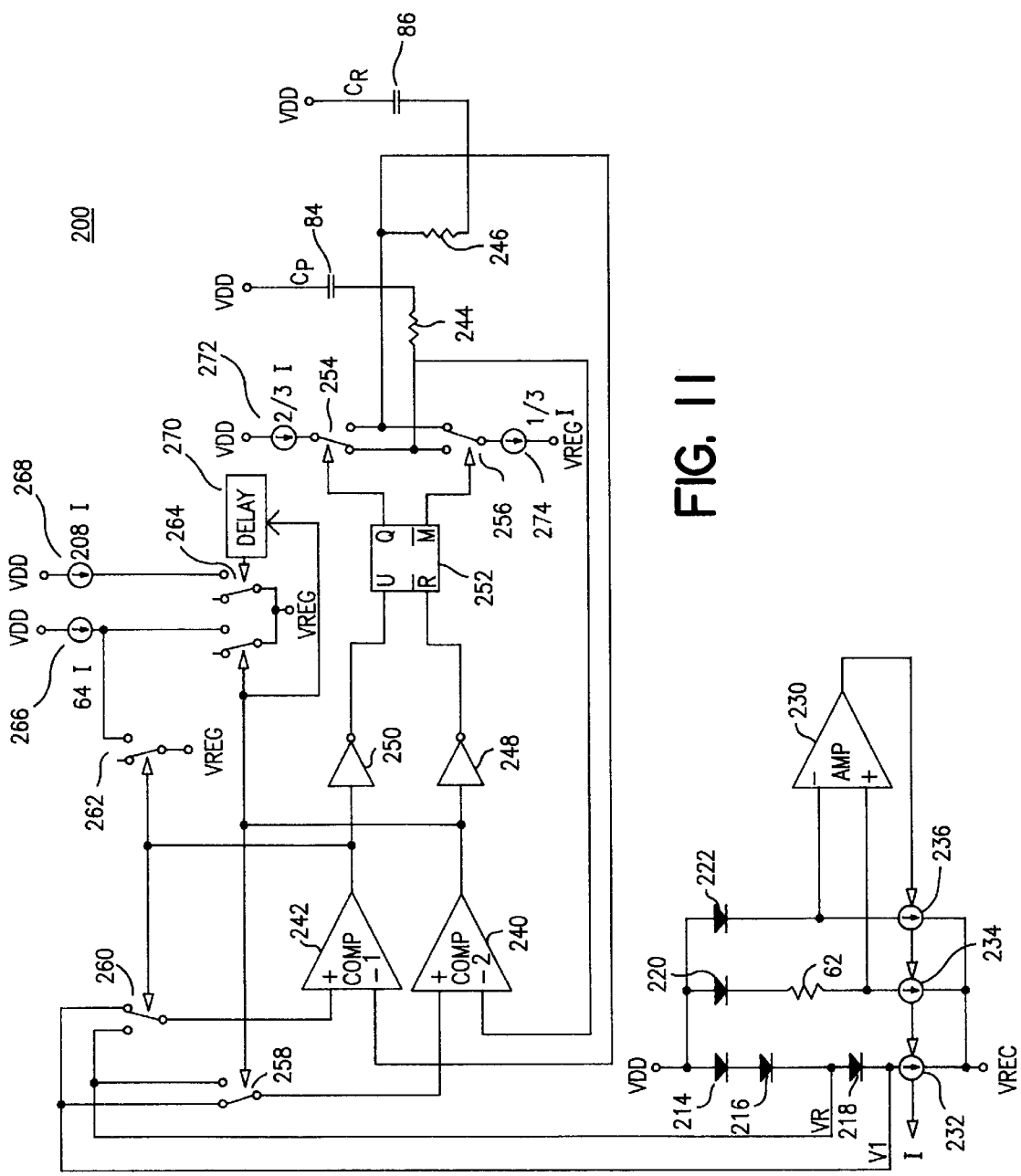
FIG. 11 is a schematic diagram of the pressure and temperature signal modulating circuit.

The pressure and temperature signal modulating sensor circuit 200 (including the circuit within the IC chip 64, the associated resistor 62 mounted on the substrate 60 and the pickoff and reference capacitors $C_P$ and $C_R$) within pressure sensing module 20 is shown in FIGS. 10 and 11. Sensor circuit 200 translates the pressure and temperature modulated pickoff and reference capacitor $C_P$ and $C_R$ values into charge time-modulated intervals Tprs and Ttemp, respectively, between sensor current pulse signals $P_R$ and $P_P$. transmitted up the active lead conductor 16.

FIG. 10 also depicts the equivalent circuit impedance of the pressure sensing lead 12 within the dotted line block denoted 12. The lead conductors 14 and 16 can exhibit a leakage resistance 202 as low as about 300 kW and capacitance 204 of about 110 pf between them. Lead conductor 14 has a series resistances 206 and 208 totaling about 25 W, and lead conductor 16 has a series resistances 210 and 212 totaling about 40 W. The leakage resistance and capacitance may deviate over the time of chronic implantation. The demodulator 150 includes lead load impedances and is calibrated at implantation in a manner described below.

The passive lead conductor 14 applies VDD from demodulator 150 to the VDD terminal of IC chip 64 and to the pickoff and reference capacitors $C_P$ and $C_R$. The active lead conductor 16 connects the terminal VREG of IC chip 64 to the terminals CPOUT and CPIN of demodulator 150 through an equivalent resistor network depicted in FIG. 13.

Figure 12:
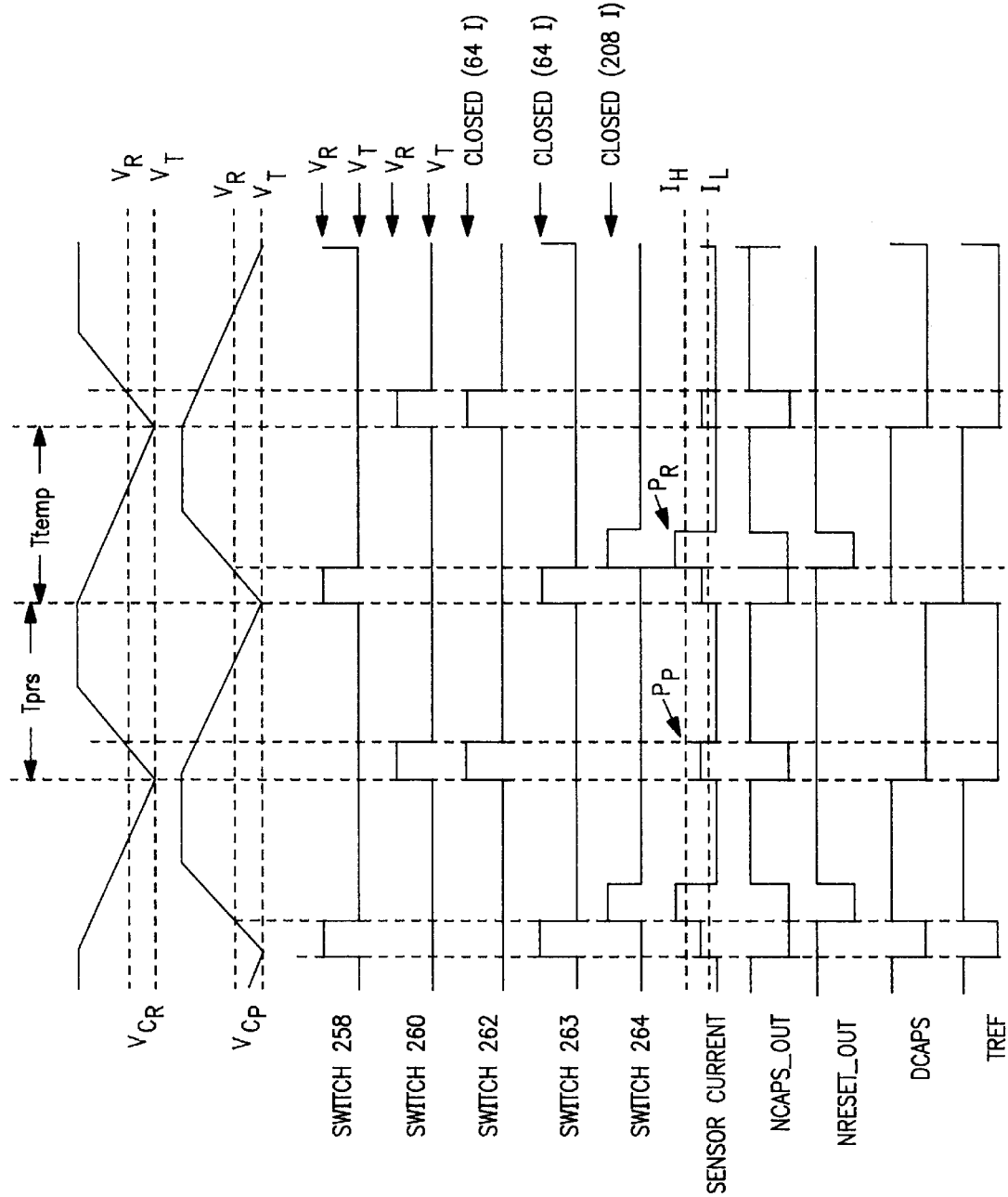
FIG. 12 is a timing diagram of the pulse signals emitted by the circuits of FIGS. 11 and 13.

The pressure and temperature signal modulating sensor circuit 200 is shown in greater detail in FIG. 11 and essentially operates as a bi-stable multivibrator operating near the target frequency of 5 kHz in alternately charging plate 86 of reference capacitor $C_R$ and plate 84 of the pickoff capacitor $C_P$ from VDD, which in this case is 0 volts, through reference voltage VR and to a target voltage VT through a current source of ⅓ I as shown in the two waveforms of FIG. 12 labeled VCR and $VC_P$. The reference capacitor $C_R$ and the pickoff capacitor $C_P$ are alternately discharged through a further current source of ⅔ I coupled to VDD through the reference voltage VR back to VDD or 0 volts as also shown in these two waveforms of FIG. 12. It should be noted that the wave forms of FIG. 12 are not to scale and are exaggerated to ease illustration of the signals generated in the sensor circuit 200 and the demodulator circuit 150.

The pickoff and reference capacitors $C_P$ and $C_R$ are both nominally 2.2 pF, but approach 3.0 pF with stray capacitances. Due to the biasing convention employed, the reference capacitor $C_R$ and the pickoff capacitor $C_P$ are considered to be discharged when their plates 86 and 84, respectively, are both at VDD or 0 volts. The common plate 51 is always at VDD or 0 volts. The reference and pickoff capacitors $C_R$ and $C_P$ are considered to be charged (to some charge level) when the plates 84 and 86 are at a voltage other than 0 volts. In this case, the charges are negative charges between VDD and VREG or between 0 and –2.0 volts. Thus, the convention employed dictates that reference and pickoff capacitors $C_R$ and $C_P$ are "charged" toward –2.0 volts and "discharged" from a negative voltage toward 0 volts.

The principle involved is also applicable to a VSS convention, where the charged voltage levels would be positive rather than negative in polarity.

Figure 13:
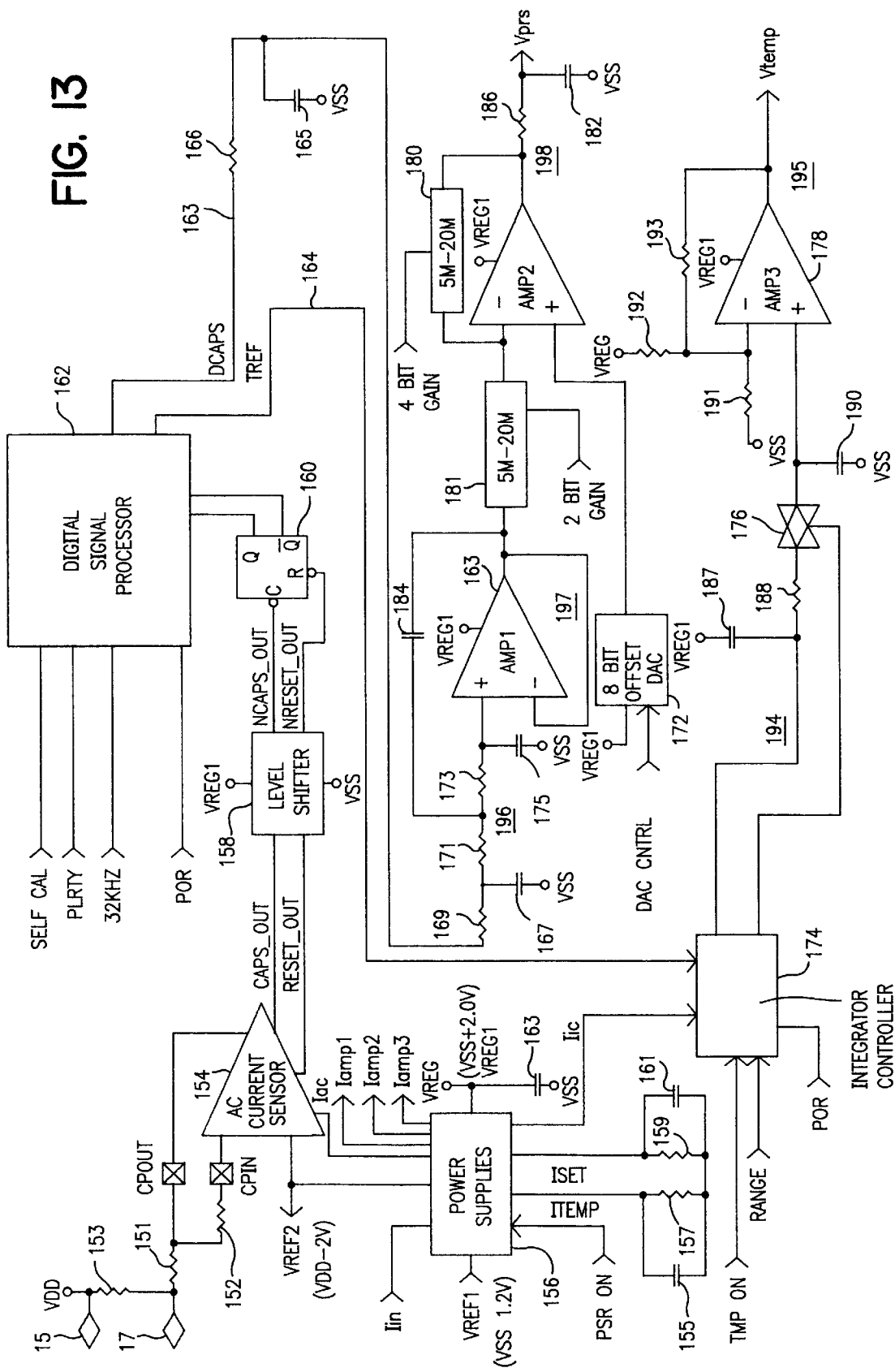
FIG. 13 is a schematic diagram of the demodulator of the pressure monitor of FIG. 1.

In practice, when demodulator 150 of FIG. 13 is powered up, it supplies the voltage VDD at 0 volts to lead conductor 14 and VREG at –2.0 volts to lead conductor 16 of the lead 12. The regulated voltages VDD and VREG supplied by the demodulator 150 to the sensor 200 of FIG. 11 are applied to a voltage dividing diode network including diodes 214, 216, and 218 and current source 232 in a first branch, diode 220, external resistor 62, and current source 234 in a second branch, and diode 222 and current source 236 in a third branch. Voltage VT is three diode forward voltage drops lower than VDD through diodes 214, 216 and 218, or about −1.5 volts, and voltage VR is two diode forward voltage drops lower than VDD through diodes 214 and 216 or about −1.0 volts.

Differential current amplifier 230 is coupled to the second and third branches and its output is applied to current sources 232, 234 and 236 in each branch. The current I is defined by the voltage difference between two diodes 220 and 222 operating at significantly different current densities, divided by the value of the chip resistor 62. Changes in ambient temperature affect the diode resistances and are reflected in the output signal from differential amplifier 230. Current sources 234, 236 are driven to correct any current imbalance, and current source 232 develops the current I reflecting the temperature change within the sensor module 20.

The principle employed in the pressure and temperature signal modulating sensor circuit 200 is a deliberate misuse of the band gap regulator concept, in that rather than using the band gap method to create a current source insensitive to temperature, the current source 232 varies a known amount, about 1% /° C., with variation in temperature. This allows the variation in the reference capacitor $C_R$ charge-modulated time Ttemp to be used as a thermometer, in the interest of correcting for sensor internal pressure change with temperature and subsequent absolute pressure error affecting the gap, and hence the capacitance, of the pickoff capacitor $C_P$. Since the gap of the reference capacitor $C_R$ cannot change significantly with pressure or temperature, the primary change in Ttemp can only occur due to temperature induced change in current I generated by current source 232.

The reference voltage VR and the target voltage VT are applied to the switched terminals of schematically illustrated semiconductor switches 258 and 260. The common terminals of semiconductor switches 258 and 260 are coupled to a positive input of comparators 240 and 242, respectively. The negative terminals of comparators 240 and 242 are coupled through the series charge resistors 244 and 246, respectively, to the plates 84 and 86 of the pickoff capacitor $C_P$ and the reference capacitor $C_R$, respectively. The outputs of the comparators 240 and 242 are inverted by inverters 248 and 250, respectively, and applied to inputs of the flip-flop 252. The outputs of the flip-flop 252 are applied to control terminals of the schematically illustrated semiconductor switches 254 and 256. Semiconductor switches 254 and 256 are bistable in behavior and alternately connect current source 272, providing ⅔ I, and current source 274, providing ⅓ I, to the reference capacitor $C_R$ and the pickoff capacitor $C_P$ depending on the state of flip-flop 252. When the current source 272 is applied to one of the capacitors, the current source 274 is applied to the other capacitor. The capacitor voltage on plate 84 or 86 is discharged through current source 272 back to VDD or 0 volts while the capacitor voltage on plate 86 or 84, respectively, is charged through current source 274 toward VT as shown in FIG. 12.

The outputs of comparators 240 and 242 are also applied to control the states of schematically illustrated semiconductor switches 258, 260, 262, 263 and 264. Semiconductor switches 258 and 260 are monostable in behavior and switch states from the depicted connection with target voltage VT to reference voltage VR each time, and only so long as, a high state output signal is generated by the respective comparators 240 and 242. The timing states of these switches 258 and 260 closed for conducting VR or VT to respective comparators 240 and 242 are also shown in the wave forms labeled 258 and 260 shown in FIG. 12.

The outputs of comparators 240 and 242 are normally low when the capacitor charge voltages $VC_P$ and $VC_R$, respectively, applied to the positive terminals are lower, in an absolute sense, than the voltages VT applied to the negative terminals.

The charging of the capacitor $C_P$ or $C_R$ coupled to the charge current source 274 to the voltage VT or −1.5 volts causes the associated comparator 240 or 242 to go high. When the comparator goes high, the flip-flop 252 changes state exchanging the closed states of semiconductor switches 254 and 256, thereby causing the previously charging (or fully charged) capacitor to commence discharging and causing the previously discharged other capacitor to commence charging.

The high output state of the associated comparator remains for a predetermined capacitor discharge time period from VT to VR providing a one-shot type, high state output. When the capacitor $C_P$ or $C_R$ voltage discharges to VR, the high state output of the respective comparator 242 or 240 is extinguished, and semi-conductor switches 258 or 260 is switched back to apply VT to the respective negative terminal of the comparator 240 or 242. However, the capacitor $C_P$ or $C_R$ continues to discharge until the plate 84 or 86, respectively, is back at full discharge or 0 volts. Since the discharge rate exceeds the charge rate, there is a period of time in each cycle that the capacitor $C_P$ or $C_R$ remains at 0 volts while the other capacitor charges toward VT (as shown in FIG. 12). This ensures that each capacitor is fully discharged to 0 volts at the start of its respective charge time interval.

As shown specifically in FIG. 11, the switches 258 and 260 are set to apply the voltage VT to comparators 240 and 242, and the switches 262, 263 and 264 are all open. The plate 84 of pickoff capacitor $C_P$ is connected with the ⅔ I current source 272 and is being discharged toward VDD, that is 0 volts, while the plate 86 of reference capacitor $C_R$ is connected with the ⅓ I current source 274 and is being charged toward VT or −1.5 volts. Because of the arrangement of the switches, 258, 260, 262, 263, and 264, no pulses are being generated. It can be assumed that the plate 84 of pickoff capacitor $C_P$ is being charged from VDD toward VR and that the voltage on the plate 86 of reference capacitor $C_R$ is discharging from VR toward VDD. When the output of comparator 242 does go high, the high state signal will cause switch 260 to switch over from the then closed pole position (e.g. the pole position schematically depicted in FIG. 11) to the other open pole position and remain there until the comparator 242 output goes low again when the capacitor voltage falls back to VT. Similarly, when the output of comparator 240 goes high in the following charge cycle, the high state signal causes switch 258 to switch over from the then closed pole position (e.g. the pole position schematically depicted in FIG. 11) to the other open pole position and remain there until the comparator 240 goes low. In this fashion, the reference voltage VR is alternately applied by switches 258 and 260, respectively, to the negative terminals of comparators 240 and 242 for the relatively short VR to VT discharge times shown in FIG. 12.

To summarize, when the charge voltage on the pickoff capacitor $C_P$ reaches VT, the comparator 240 switches its output state high, in turn changing the state switch 258 and closing switch 263. Delay circuit 270 is enabled to close switch 264 when switch 263 re-opens. Similarly, in the next cycle, when the voltage on reference capacitor $C_R$ reaches VT, the comparator 242 switches its output state high, changing the state of switch 260 and closing switch 262.

Normally open semiconductor switches 262 and 263 are also monostable in behavior and are closed for the duration of the comparator high state, that is, the VT to VR discharge time period. When closed, the timing current pulses $P_R$ and $P_P$ separating (at their leading edges) the reference and pickoff charge-time modulated intervals Ttemp and Tprs also shown in FIG. 12 are generated.

The timing current signal pulse $P_P$ is controlled in width by the reference capacitor $C_R$ capacitor discharge time from VT to VR as shown in the Sensor Current line of FIG. 12. The initial low amplitude step of two step timing current signal pulse $P_R$ is also controlled in width by the reference capacitor $C_R$ capacitor discharge time from VT to VR as shown in the wave form labeled Sensor Current in FIG. 12. The VT to VR discharge times, which govern the closed time periods of switches 258 and 260 and the widths of the low amplitude steps of the timing current pulses $P_R$ and $P_P$, are nominally 8–12 msec. The high amplitude step of two step timing current signal pulse $P_R$ is controlled in width by delay circuit 270 of FIG. 11.

The high state signal output of comparator 242 therefore closes normally open switch 262 for the duration of the high state, i.e. the VT to VR discharge time of reference capacitor $C_R$. When switch 262 closes, the current source 266 providing 64 I is applied to the VREG terminal, resulting in the generation of the timing current pulse $P_P$ depicted in FIG. 12 appearing on conductor 16 as a sensor current. Similarly, the high state signal output of comparator 240 also closes the normally open switch 263 for the VT to VR discharge time of duration of pickoff capacitor $C_P$ and is applied to the delay circuit 270. Delay circuit 270 effects the closure of switch 264 at the end of the high state and then maintains closure of the switch 264 through a delayed high state time period. When switches 263 and 264 are sequentially closed, the current source 266 providing 64 I is applied to the VREG terminal, and then the current source 268 providing 208 I is applied to the VREG terminal. In this manner, the stepped current timing pulse $P_R$ depicted in FIG. 12 is generated.

The nominal pulse height of 8.0 mA for timing current pulse $P_P$ and for the initial step of timing current pulse $P_R$ is effected by the 64 I current source 266 when either switch 262 or 263 is closed. The nominal, pulse height of 24.0 mA (stepped up from the initial 8.0 mA step) of pulse $P_R$ is effected by the 208 I current source when switch 264 is closed after switch 263 reopens. Between pulses, a baseline supply current of 1.5 mA is present at VREG and on lead conductor 16 to which the current pulse heights or sensor current amplitudes are referenced.

The 8.0 mA leading step of pressure-related timing current pulse $P_P$ matches the slew rate of the 8.0 mA peak of temperature-related, reference timing current pulse $P_R$, which reduces errors that would otherwise be associated with detection of different amplitude pulses having differing slew rates. The rise time of both of the pulses appears to be the same to the current sensor 154 in the demodulator 150. The start of each pulse can therefore be accurately detected and employed as the start and end times for the intervening charge time intervals Tprs and Ttemp. The differing peak amplitudes of the two pulses are readily distinguishable to determine the order of the intervals.

Thus, FIG. 12 illustrates the waveforms at the switches 258, 260, 262, 263 and 264 in relation to the charge and discharge voltage waveforms of the reference and pickoff capacitor $C_R$ and $C_P$ as well as the timing current pulses $P_P$ and $P_R$ generated at the terminal VREG marking the starts of the respective capacitor charging intervals Tprs and Ttemp.

At 37° temperature and a barometric pressure of 740 mm Hg, the capacitance values of capacitors $C_P$ and $C_R$ are approximately equal. Therefore, both capacitors $C_P$ and $C_R$ charge at an approximately equal rate. The intervals between timing signal pulses $P_P$ and $P_R$ are approximately equal, reflecting a 50% duty cycle (calculated as the ratio of Tprs to Ttemp+Tprs), and the nominal operating frequency from $P_P$ to $P_P$ is 5 kHz.

After implantation, the temperature should vary somewhat from 37°. The current I, which changes with temperature change, affects the charge times Ttemp and Tprs equally which changes the operating frequency. In addition, the intracranial fluid pressure change between the cerebral equivalent of "systole" and "diastole" may conceivably alter the capacitance of the pickoff capacitor $C_P$ which only affects the charge time Tprs. Thus, charge time Ttemp only changes with temperature, and the combined result is a change in frequency and duty cycle dependent on both temperature and pressure changes.

The schematically illustrated current sources and semiconductor switches may be readily realized with conventional integrated circuit designs.

Demodulator Circuit

The demodulator 150 shown in FIG. 13 supplies the voltages VDD and VREG, at a baseline current drain from sensor IC chip 64 of about 1.5 mA, to the lead conductors 14 and 16 and receives the timing signal current pulses $P_P$ and $P_R$ modulating the baseline current on conductor 16. The demodulator 150 converts the charge time intervals Tprs and Ttemp separating the leading edges of the train of current pulses of FIG. 12 into voltage signals Vprs and Vtemp, respectively. The voltage signals Vprs and Vtemp are supplied to the digital controller/timer circuit 132 and are converted by ADC/MUX circuit 142 into digital values representing absolute pressure and temperature data, which are stored in the microcomputer circuit 114 in a timed relationship with other monitored physiologic data.

As described above, the analog temperature signal Vtemp is derived from the interval Ttemp between the leading edges of $P_R$ and $P_P$ in an integration process, and the analog pressure signal Vprs is derived from the interval Tprs between the leading edges of $P_P$ and $P_R$ in a duty cycle signal filtering and averaging process. In these processes, the demodulator 150 creates the intermediate voltage square waves NCAPS_OUT, NRESET_OUT, and DCAPS shown in FIG. 12 from the current pulse timing intervals. The voltage signal Vtemp can be determined from a relatively simple integration of a time interval related to the time interval Ttemp. The voltage signal Vprs is derived by low pass filtering the square waves of the DCAPS signal representing the time intervals Tprs and Ttemp to obtain the average voltage.

The temperature related capacitance changes are specified to be in a narrow range of 37° C. ±5° C. which could effect an ideal gas law pressure variation of 20 mm Hg full scale over the 10° C. temperature change. The limited range of the A/D conversion provided by the ADC/MUX circuit 142 and the trimmed slope of the temperature channel integrator causes a Ttemp to range between 66 msec to 116 msec in a first range and between 96.5 msec to 146.5 msec in a second range. The resulting voltage range of the analog signal Vtemp produced at the output of the temperature processing channel is specified to be from 0 to 1.2 volts to be processed by the ADC/MUX circuit 142.

The blood, ambient (atmospheric, altitude, meteorologic) pressure changes affecting the pickoff capacitor are specified in a preferable total range of 400 to 900 mm Hg. The DAC offset adjustment allows the pressure system to be adjusted under user and/or software control to provide this total range in order to be compatible with the more limited range of the 8 bit A/D converter.

In practice the gain of the pressure system will be adjusted dependent on the sensitivity of the particular pressure sensor in order to provide an A/D pressure "range" that encompasses the expected intracranial or body fluid pressure range of the patient plus expected local meteorologic pressure changes and expected altitude pressure changes seen by the patient. The intracranial fluid pressure is normally expected to range between 0 and 40 mm Hg of gage pressure (relative to atmospheric or barometric pressure).

The resulting voltage range of the analog signal Vprs produced at the output of the absolute pressure signal processing channel is also specified to be from 0 to 1.2 volts to be processed by the ADC/MUX circuit 142.

Turning again to the demodulator circuit 150 of FIG. 13, it receives a number of biasing and command signals from the digital controller/timer circuit 132, supplies the voltages VDD and VREG to the pressure and temperature signal modulating circuit 200, processes the sensor current pulses $P_R$ and $P_P$. and provides the analog signals Vtemp and Vprs to the digital controller/timer circuit 132. Commencing first with the biasing and operating input signals, the demodulator circuit 150 receives the regulated voltage signal VREF1 at +1.2 volts, a current signal Iin of 20 nA, and a command signal PSR ON at the power supply 156. The regulated voltage VREF1 is the same reference voltage as is employed by the ADC/MUX circuit 142 for digitizing the analog voltage signal between 0 and +1.2 volts into an 8-bit digital word having 0–255 values. The output signals Vprs and Vtemp therefore must fall in this range of 0–1.2 volts to be processed. It is simpler then to develop accurate regulated voltages and currents of the demodulator 150 from that same regulated voltage. In addition, it should be noted that the demodulator circuit 150 as well as the other circuits of the monitor 100 including the microcomputer circuit 114 are referenced to VSS or battery ground which is at 0 volts. Therefore, the conventions are reversed from those prevailing in the sensor circuit 200. It will be understood that the same convention could be used in both cases.

From this source, the power supply 156 develops the voltage VREF2 at –2.0 volts below VDD (VDD–2.0 volts), VREG1 at +2.0 volts, and the regulated current signals Iac, lamp1, lamp2, lamp3, and Iic that are applied to the circuit blocks of FIG. 13. The off-chip capacitor and resistor networks 155,157 and 159, 161 provide bias controls ITEMP for the current Iic and ISET for the current Iac, respectively. The resistor 159 is selected to provide the Iac current to develop specific current thresholds described below for the AC current sensor 154. The resistor 157 is trimmed at the manufacture of each monitor 100 to provide a specific current level Iic for the integrator controller 174.

The POR and 32 kHz clock signals are applied on power-up of the monitor 100. The command signal PSR ON, and other command signals TMP ON, 2-BIT GAIN, 4-BIT GAIN, 8-BIT DAC CNTRL, SELF CAL, PLRTY and RANGE are provided to the demodulator circuit 150 by the digital timer/controller circuit 132 from memory locations within the microcomputer circuit 114. Programmed-in commands dictate the operating states and parameters of operation reflected by these command signals. Command signal values and states are stored in microcomputer 114 in memory locations that are accessed from the digital timer/controller circuit 132 and supplied to the demodulator circuit 150 in three words. A GAIN word of 6 bits (2-BIT GAIN & 4-BIT GAIN), a DAC word of 8 bits and a CONTROL word of 6 bits (POR, PSR ON, TMP ON, SELF CAL, RANGE, PLRTY) are stored to set the operating states and selected parameters of operation.

For example, the pressure and temperature sensing functions can be separately programmed ON or OFF or programmed ON together by the PSR ON and TMP ON signals. The 1-bit PSR ON command enables the bias currents lamp1, lamp2, lamp3 to operate the pressure signal processing channel. The 1-bit TMP ON command enables the integrator controller 174 to operate the temperature signal processing channel. The remaining command values and states will be explained in context of the components of the demodulator circuit 150.

Turning to the processing of the sensor current pulses $P_P$ and $P_R$, the lead conductor 14 is connected to the connector block terminal 15 which is also connected to VDD. The lead conductor 16 is connected to the VREG connector block terminal 17. A load resistor 153 is coupled across connector block terminals 15 and 17 and between VDD and VREG in order to obtain a 2.0 volt drop and to reduce the effects associated with changes in the lead leakage resistance 202. The lead conductor 16 at connector block terminal 17 is connected through resistors 151 5. and 152 to one input terminal CPIN of the AC current sensor 154 and through resistor 151 alone to the output terminal CPOUT connected to a current sink in the AC current sensor 154.

A further input terminal of AC current sensor 154 is connected to the voltage VREF2 at (VDD–2.0) volts developed by power supply 156. The current sensor 154 operates as a voltage regulator for ensuring that the voltage at CPOUT remains at VREF2 or (VDD–2.0) volts at all times, regardless of the effect of the current pulses $P_P$ and $P_R$ generated during charge of the capacitors $C_P$ and $C_R$ as described above and appearing on conductor 16 at connector block terminal 17. Since the voltage drop across resistor 151 is small, VREG of the circuit 200 in FIG. 11 may be viewed as VREF2 of the demodulator circuit 150 of FIG. 13. Resistor 151 provides protection against external overdrive due to electromagnetic interference or cardioversion/defibrillation pulses.

The current sensor 154 also includes comparators established by the current Iac that discriminate the amplitudes of current pulses $P_P$ and $P_R$ when they appear and generate the output signals CAPS_OUT and RESET_OUT. The signal amplitudes are discriminated and reduced to current levels established by the comparators and reference current sources in AC current sensor 154. The CAPS_OUT signal is developed in response to both of the low and high amplitude current pulses $P_R$, and the RESET_OUT signal is developed in response to the high amplitude current pulse $P_R$ only.

The discrimination of the distinguishing parameters of the current pulses $P_P$ (8.0 mA) and $P_R$ (8.0 mA followed by 24.0 mA) is effected by amplitude comparators in AC current sensor 154 that are set by current Iac provided by power supplies 156. The resistor 159 determines the current ISET which in turn determines the current Iac and the thresholds for the input current pulses in the AC current sensor 154. Preferably, a low current threshold $I_L$ of +3.6 mA and a high current threshold $I_H$ of +14.4 mA are established for the 8.0 mA and 24.0 mA nominal current pulse amplitudes. The ratio of these two thresholds cannot be changed, but their values are set by resistor 159 to allow for variances in the actual peak step amplitudes of the current pulses $P_P$ and $P_R$.

A sensor current pulse $P_P$ or $P_R$ having a step that exceeds the $I_L$ (+3.6 mA) low threshold generates an output signal at CAPS_OUT, whereas the high step of current pulse $P_R$ that exceeds the $I_H$ (+14.4 mA) high threshold generates an output signal at RESET_OUT. The CAPS_OUT and RESET_OUT signals are applied to the level shifter 158 which responds by normalizing the signals between VSS or 0 volts and VREG1 of +2.0 volts and providing the NCAPS_OUT and NRESET_OUT signals shown in FIG. 12. The normalized NCAPS_OUT and NRESET_OUT signals are applied to the clock and reset inverting inputs, respectively, of flip-flop 160. The inverting inputs effectively invert the depicted NCAPS_OUT and NRESET_OUT signals shown in FIG. 12. The flip-flop 160 responds by providing a square wave output signal CAPS (not shown in FIG. 12) at its Q-output that is high during the interval Tprs and low during the interval Ttemp.

In the decoding of the Ttemp and Tprs intervals from the current pulse peaks $P_P$ and $P_R$, the NCAPS_OUT signal is applied to inverting clock input of flip-flop 160 to cause it to switch state. The NRESET_OUT signal is applied to the inverting reset input of flip-flop 160 and does not cause it to change state when its state at the Q output is already low. If, however, the Q output state is high on arrival of NRESET_OUT, the flip-flop 160 state is switched low, resulting in the high state of the DCAPS square wave signal as shown in the first instance in FIG. 12. The high amplitude phase of current pulse $P_R$ therefor synchronizes the state of the DCAPS square wave signal on power up and restores any loss of synchronization that may occur from time to time. Once synchronization is established, each successive 8 mA step of the respective current pulse peaks $P_P$ and $P_R$ shown in FIG. 12 switches the Q output state of the flip-flop 160, causing the square wave of the CAPS and DCAPS signals reflecting the Ttemp and Tprs intervals.

The CAPS square wave output signal is applied to a digital signal processor 162 and is normally inverted to provide the DCAPS signal shown in FIG. 12 at a first output. The digital signal processor 162 also normally inverts the CAPS signal to provide the TREF signal at a second output. In this fashion, the Tprs interval of DCAPS provided to the input of pressure signal processing channel 163 is negative in polarity, and the Ttemp interval of TREF provided to the input of the temperature signal processing channel 164 is positive in polarity. In regard to the polarities of signals DCAP and TREF, the digital signal processor 162 also receives the PLRTY signal from the digital controller/timer circuit 132. The PLRTY signal may be selectively programmed to invert the polarity of the DCAPS square wave in order to increase the operating range of the pressure signal processing channel 163. However, it is expected that the PLRTY signal would seldom be changed, and such a programming option may be eliminated if the range provided in the pressure signal processing channel 163 is sufficient.

As described further below, a self calibration mode can be initiated in response to a SELF CAL signal to apply a 5.46 kHz square wave signal through the digital signal processing circuit 162 to the temperature integrator controller 174 for calibration purposes. The 5.46 kHz square wave signal is simply chosen for convenience, since it is an even sub-multiple of the 32 kHz clock frequency and is close to the nominal 5 kHz operating frequency. The following discussion assumes first that the temperature processing channel 164 is already calibrated in the manner described below and that the normal operating mode is programmed (SELF CAL off) so that only the CAPS signal is processed by the digital signal processor 162.

Addressing the derivation of the signal Vtemp by the temperature signal processing channel 164 first, the temperature is demodulated from the high state of the TREF square wave signal having a duration directly relating to the charge time Ttemp. The integrator controller 174 employs the current Iic to charge an integrator capacitor 187 over the time Ttemp (or a portion of that time as explained below) and then charges sample and hold capacitor 190 to the voltage on integrator capacitor 187. The voltage on integrator capacitor 187 is then discharged and the voltage on sample and hold capacitor 190 is amplified by temperature amplifier stage 195 to become the Vtemp signal in the range of 0–1.2 volts.

More particularly, when the integrator capacitor 187 is not being charged or the voltage transferred to the sample and hold capacitor 190, both plates of the integrator capacitor 187 are held at VREG1 and the bidirectional switch 176 is open. Again, the discharge state is characterized as a state where there is no net voltage or charge on the capacitor 187, and the charged state is characterized by a net voltage difference across its plates, even though the "charged" voltage may be nominally lower than the "discharged" voltage.

When the TREF signal goes high (and the low range is programmed), the integrator controller 174 commences charging the plate of integrator capacitor 187 connected to resistor 188 to a voltage lower than VREG1 through a current sink to VSS internal to integrator controller 174. At the end of the high state of the TREF signal, the current sink to VSS is opened and the bidirectional switch 176 is closed for one clock cycle time (30.5 msec) to transfer the resulting voltage level on capacitor 187 to capacitor 190. Bidirectional switch 176 is then opened, and capacitor 187 is discharged by setting both plates to VREG1 through switches internal to integrator controller 174. With each successive recharge of integrator capacitor 187, the capacitor 187 voltage level achieved varies upward and downward from its preceding voltage level with changes in the width of the high state of the TREF signal, and the new voltage level is transferred to capacitor 190. The new voltage level is held on capacitor 190 when the switch 176 is opened.

The switching of bidirectional switch 176, resistor 188 and capacitor 190 also form a low pass filter. The pass band of this filter is sufficient to allow only the temperature related component of the signal to pass through and be reflected on capacitor 190.

The resulting voltage on capacitor 190, amplified by amplifier stage 195, provides the Vtemp signal representing the temperature in the pressure sensor cavity. Amplifier stage 195 includes an amplifier 178 referenced back to approximately +1.2V through the voltage divider comprising resistors 191, 192, 193 dividing the VREG1 of +2.0 volts. Amplifier stage 195 has a gain of two, and so the maximum voltage which the sample and hold capacitor 190 can reach is +0.6V. This corresponds to a +0.6 volt level on integrating capacitor 187 at its junction with resistor 188 which is achieved in 116 msec employing the regulated current Iic.

Two operating ranges provide a higher resolution of the possible values of the reference capacitor$_R$ charging time Ttemp reflected by the high state of the TREF signal. Either a high or low range must be programmed by the RANGE bit based on individual sensor circuit 200 characteristics and/or the temperature range of the patient. Since a 5° C. change in temperature will result in approximately 5% change in Ttemp, the 8-bit ADC count provided by ADC/MUX circuit 142 in response to Vtemp for a particular lead cannot be near the limits of 0 and 255.

For this reason, both the high range and low range for the temperature are provided, and one or the other is selected via a one-bit value of the above-referenced 6-bit CONTROL word. Setting the RANGE bit to 1 places integrator controller 174 in the high range mode which corresponds to a TREF high state pulse width of 96–146 msec. Programming the RANGE bit to 0 places integrator controller 174 in the low range mode which corresponds to a TREF high state pulse width of 66–116 msec. The limit of 0.6 volts can be reached at the upper end of this pulse width range.

However, it is anticipated that the high operating range will be necessary in certain instances. When the high range mode is selected, the integrator controller 174 effectively prolongs the high state TREF square wave by delaying the charging of the integrator capacitor 187 by one clock cycle or 30.5 msec from the beginning of the high state TREF square wave. This effectively shortens the TREF high state pulse width range of 96–146 msec that is integrated back to 66–116 msec, allowing the Vtemp voltage signal to fall into the 0–0.6 volt range that can be doubled in amplifier stage 195, digitized and stored. The programmed range is also stored with the digitized temperature data so that the proper values can be decoded from the telemetered out data.

In order to set the RANGE for proper temperature measurement in a given patient, one or the other range is programmed and the digitized temperature readings are accumulated and telemetered out. If they are in a proper range, then the programmed RANGE is correct. In general, if in the low range mode and if the digital temperature value is a digital word 50 or less, it is necessary to program the high range. And, if in high range mode and the digital word is 200 or more, it is necessary to program to the low range. Alternatively, the range could be automatically switched at these threshold levels.

The rate of charge of integrator capacitor 187 in these ranges to get to the proper voltage range of 0–0.6 volts depends on the current Iic. The self calibration of the temperature signal processing channel 164 is necessary to trim the resistor 157 to precisely set the current ITEMP and the current Iic so that a voltage of 0.590 volts is reached on capacitor 187 after a 116 msec integration time. In this mode, the RANGE is programmed to the low range, and the SELF CAL signal is programmed ON. The digital signal processor 162 responds to the SELF CAL ON signal to divide the 32 kHz clock signal provided from digital controller/timer circuit 132 by 6 into a 5.46 kHz square wave signal exhibiting a 50% duty cycle. The digital signal processor substitutes the square wave calibration signal for the TREF signal and applies it to the temperature signal processing channel 164 and to the input of the integrator controller 174. The resistance of resistor 157 is trimmed to adjust integrator current Iic until the voltage 0.590 volts is achieved in 116 msec or an ADC count of 125 is reached.

Turning now to the derivation of the pressure signal Vprs, the nominally 5 kHz DCAPS positive and negative square wave of +2.0 volts is filtered and averaged to derive a voltage signal Vprs in the range of 0–1.2 volts at the junction of capacitor 182 and resistor 186. The 5 kHz signal component is filtered out by a 4-pole filter including a 250 Hz low pass filter provided by capacitor 165 and resistor 166, an active Butterworth filter comprising 40 Hz low pass filter network 196 and first pressure amplifier stage 197, and a further 1 pole, 250 Hz low pass filter pole comprising capacitor 182 and resistor 186. The low pass filter network 196 comprises the resistors and capacitors 165 –167, 169, 171, 173, 175, 182 and 186 and averages the voltage square wave to create a D.C. voltage proportional to the DCAPS square wave signal duty cycle. The first pressure amplifier stage 197 buffers the filtered pressure-related signal at its output. The filtered output signal is applied to second, inverting, pressure amplifier stage 198 which comprises the amplifier 170 and the programmable gain, switched resistor networks 180 and 181. Amplification and voltage offset of the output signal of amplifier 168 is provided in second pressure amplifier stage 198 by the 2-BIT GAIN, 4-BIT GAIN and 8-bit offset DAC settings.

The variations in the manufacturing tolerances and conditions of the sensor module 20 affects the reference and pickoff capacitance values and the response to temperature and pressure changes that particularly affect the pressure sensing function. The gain and offset adjustments are provided to correct for such affects. The offset adjustment is also required to provide for pressure range adjustments so that the pressure range used provides adequate resolution of pressure differences. As mentioned above, the AND conversion range of the ADC/MUX circuit 142 is limited to 256 digitized values from a voltage range of 1.2 volts. Therefore, it is necessary to compensate for variations in the patient's own intracranial or body fluid pressure range as well as prevailing atmospheric pressure primarily related to the altitude that the patient normally is present in. These compensations are included in an offset factor developed at the time of implant.

The offset factor is provided by the 8-bit offset digital to analog converter (DAC) 172 which provides an offset analog voltage dependent on the programmed value of the DAC CNTRL binary coded digital word. The primary function of the DAC 172 is to provide the analog voltage to "zero" the offset in the system in order to keep the pressure signal within the range of the ADC/MUX block 142 (0–1.2 volts). The analog offset voltage is applied to differential pressure amplifier 170 where it is subtracted from the output voltage of the first pressure amplifier 168. The total programmable range of the DAC 172 is 630 mV, between 570 mV to 1,200 mV.

The gain settings for the second pressure amplifier stage 198 can be adjusted by programming values for the 4-BIT GAIN and 2-BIT GAIN binary words stored in the RAM 124 of FIG. 1 by the external programmer. The 4-BIT GAIN signal controls the gain of the pressure amplifier stage 198 by setting switched resistors in feedback switched resistor network 180 to the binary coded gain word to provide a gain range that is selectable by the further 2-BIT GAIN signal setting of switched resistor network 181. The gain setting can be varied from 5×–20× in 1× increments, 10×–40× in 2× increments and 20×–80× in 4× increments. The gain ranges and increments are established by the 2-BIT GAIN control signal applied to the series switched resistor network 181.

The first pressure amplifier stage 197 responds to the ratio of Ttemp to the sum of Ttemp and Tprs resulting in a first filtered voltage signal. The second pressure amplifier stage 198 amplifies and inverts the first voltage signal as a function of the offset and gain settings and therefore responds effectively to the ratio of Tprs to the sum of Ttemp and Tprs, or the duty cycle of Tprs. The output signal from amplifier 170 of the second amplifier stage 198 is applied to a further low pass filter stage comprising resistor 186 and capacitor 182 to filter out any remaining component of the about 5 kHz oscillation frequency and/or any noise. The resulting filtered signal is applied as pressure signal Vprs to the digital controller/timer circuit 132 of FIG. 1.

The resulting Vprs and Vtemp voltage signals are digitized in the ADC/MUX circuit 142 in a manner well known in the art to provide digitized Vprs and Vtemp data values. The digitized Vprs and Vtemp data values are applied on bus 130 to the microcomputer circuit 114 for storage in specified registers in RAM/ROM unit 128. The digitized Vtemp data value may be employed in processing the digitized data values telemetered out by the external programmer to compensate for the temperature induced affects on the Vprs data values.

Figure 15A:
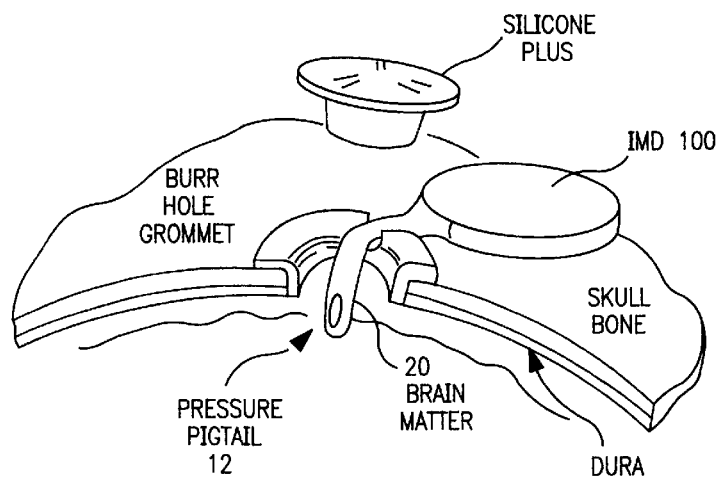
FIGS. 15(a) through 15(c) show some alternative embodiments of implantable intracranial devices and systems of the present invention.
Figure 15B:
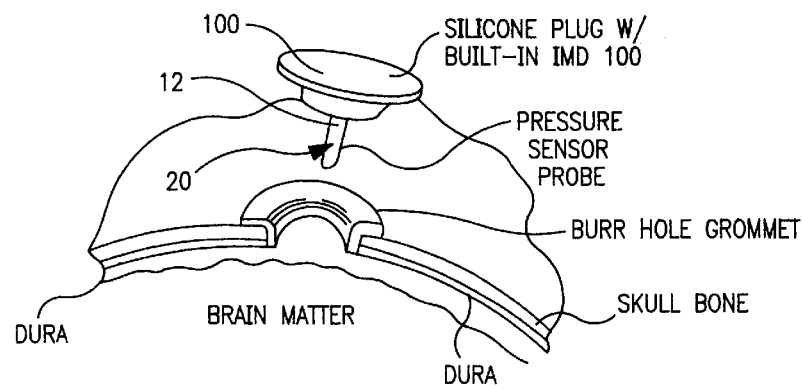
Figure 15C:
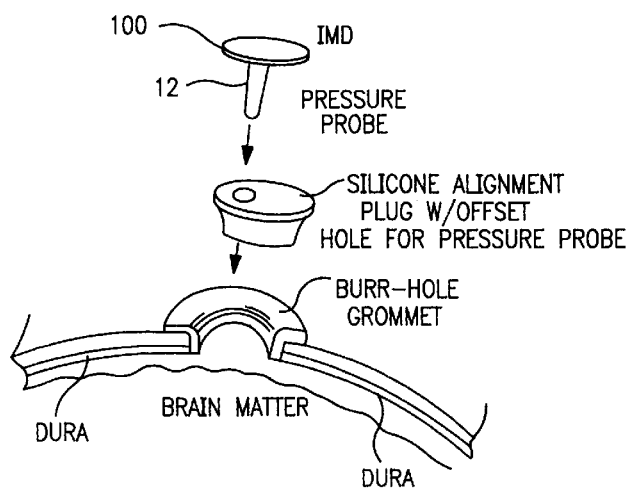

FIGS. 15(a) through 15(c) show some alternative embodiments of implantable intracranial devices and systems of the present invention. In FIG. 15(a), IMD 100 is implanted subcutaneously near a burr hole disposed in a patient's skull. The distal end of pigtail or lead 12 is disposed through the burr hole or burr hole grommet such that sensor 20 may measure or monitor intracranial fluid pressure, temperature or any other suitable physiologic parameter within or near the brain. The proximal end of pigtail or lead 12 is connected to IMD 100. A silicone plug is employed to seal the distal end of lead 12 within skull and facilitate anchoring of lead 12 to the skull.

FIG. 15(b) shows another embodiment of an intracranial fluid pressure monitoring device, where IMD 100, lead 12 and a silicone plug essentially form a structurally unitary device where lead 12 projects a short distance downwardly from the underside of IMD 100. This embodiment of the present invention is small and easier to implant than other embodiments of the present invention disclosed hereinabove. IMD 100 of FIG. 15(b) contains at least the electronic and electrical circuitry and a source of electrical energy sufficient to permit IMD 100 and lead 12 to act as a system for acquiring and telemetering on the fly data acquired by sensor 20. IMD 100 of FIG. 15(b) may be configured to feature even more sophisticated functionalities, such as storing data for later retrieval, calculating intracranial gage pressure, and controlling, directing or causing the application of a therapy.

FIG. 15(c) shows another embodiment of an intracranial fluid pressure monitoring device, where IMD 100 and lead 12 essentially form a structurally unitary device where lead 12 projects a short distance downwardly from the underside of IMD 100. In this embodiment of the present invention, the silicone plug is a separate, discrete element through which lead 12 is disposed. IMD 100 of FIG. 15(c) contains at least the electronic and electrical circuitry and a source of electrical energy sufficient to permit IMD 100 and lead 12 to act as a system for acquiring and telemetering on the fly data acquired by sensor 20.

Note that the embodiments of the present invention shown in FIGS. 15(a) through 15(c) may be configured for use in conjunction with any of the elements, components or systems disclosed in FIGS. 1a through 1d. Moreover, most of the embodiments of the present invention disclosed hereinabove may be configured or adapted to operate in conjunction with a subcutaneously disposed barometric or atmospheric pressure sensor instead of an external barometric or atmospheric pressure sensor. Such a subcutaneous barometric or atmospheric pressure sensor may be incorporated into or form a portion of IMD 100 or some portion of lead not disposed within a patient's skull.

The sensors discussed hereinabove with reference to FIGS. 1 through 15 have been described in a generic manner, since it is intended that any suitable implantable physiologic sensor may be incorporated as part of a sensor assembly according to the present invention. The following list of sensor types is provided to illustrate various known implantable physiologic sensors that are well suited for incorporation into a sensor assembly of the present invention. It is to be understood that this non-exhaustive list of sensor types is provided for illustrative purposes only, and is not intended to limit the type of sensor that may be employed in conjunction with the present inventions disclosed herein.

Such sensors include, but are not limited to, capacitive absolute pressure sensors; optical based oxygen saturation sensors; piezo-resistive absolute pressure sensors; relative pressure sensors; acceleration or activity sensors; electrochemical sensors, such as oxygen sensors and glucose sensors; Doppler flow sensors; strain gauge sensors; and electronic thermo-dilution sensors.

As discussed hereinabove, in one embodiment of the present invention sensor assembly 17 includes a pressure sensor 19 and an oxygen saturation sensor 20. An exemplary capacitive absolute pressure sensor well suited for use in sensor assembly 17 is described in U.S. Pat. Nos. 5,535,752 and 5,564,434, both of which are issued to Halperin et al. and incorporated herein by reference in their respective entireties. It should be noted that the capacitive absolute pressure sensor disclosed in U.S. Pat. Nos. 5,535,752 and 5,564,434 is a single sensor that monitors two distinct physiologic parameters, namely, an absolute blood pressure parameter and a blood temperature parameter.

As discussed hereinabove, sensor assembly 17 may include pressure sensor 19 in combination with oxygen sensor 20. An exemplary oxygen saturation sensor well suited for use in sensor assembly 17 is described in U.S. Pat. Nos. 4,750,495 and 4,903,701, both of which are issued to Moore et al. and incorporated herein by reference in their respective entireties.

The preceding specific embodiments are illustrative of the practice of the invention. It is to be understood, therefore, that other expedients known to those skilled in the art or disclosed herein may be employed without departing from the invention or the scope of the appended claims. For example, the intracranial monitoring system comprising IMD 100, lead 12 and external device may be adapted to include other features and sensing or therapy delivering capabilities such as intracranial, spinal cord and/or nerve stimulation means such as those disclosed in U.S. Pat. No. 5,683,422 to Rose; U.S. Pat. No. 5,716,377 to Rise; U.S. Pat. No. 5,792,186 to Rise et al.; and U.S. Pat. No. 5,833,709 to Rise et al., all hereby incorporated by reference herein, each in its respective entirety. As further examples, IMD 100 or other portions of the system of the present invention may include at least some of the features disclosed in U.S. Pat. No. 5,199,428 to Obel et al., U.S. Pat. No. 5,207,218 to Carpentier et al. or U.S. Pat. No. 5,330,507 to Schwartz, or U.S. Pat. No. 5,331,966 issued to Bennet et al., all of which are hereby incorporated by reference herein, each in its respective entirety.

The present invention is not limited to the use of pressure or temperature sensors employed intracranially in conjunction with IMD 100, but may be used in conjunction with other implantable and non-implantable medical devices as well such as shunts, valves and catheters, or such as electrical field sensing electrodes, neurological activity sensing electrodes, pH sensors, oxygen sensors, activity sensors, accelerometers, and so on.

The present invention is also not limited to specific data acquisition and communications techniques, such as those presented herein, but such functions may be directed using other suitable techniques. The present invention further includes within its scope methods of using IMD 100, lead 12 and external device 500, as well as the other particular structures described hereinabove.

All patents and printed publications referenced hereinabove are hereby incorporated by reference into the specification hereof, each in its respective entirety.

What is claimed is:

1. A system for measuring intracranial fluid pressure in a patient, the system comprising:
    (a) a subcutaneously implanted hermetically sealed implantable medical device;
    (b) a lead coupled to the implantable medical device having a capacitive pressure sensor for measuring absolute intracranial fluid pressure;
    (c) an external device having a barometric pressure sensor;
wherein the external device and the implantable medical device are configured to communicate telemetrically with one another such that the external device may uplink data sensed, stored or processed by the implantable medical device, a proximal end of the lead being configured for attachment to the implantable medical device, the capacitive pressure sensor being configured to receive electrical power from an electrical energy source disposed within the implantable medical device, the capacitive pressure sensor having a metal diaphragm for sensing pressure and generating signals representative thereof, electrical and electronic circuitry being disposed within the implantable medical device and configured to receive signals generated by the capacitive pressure sensor; and wherein the implantable medical device is configured to combine first data representative of the intracranial fluid pressure signals and second data representative of the barometric pressure signals to derive third data representative of intracranial gage pressure.

2. The system of claim 1, wherein the external device is a programmer.

3. The system of claim 1, wherein the metal for forming the metal diaphragm is selected from the group consisting of titanium, nobium, tantalum, gold, stainless steel, and combination or alloys thereof.

4. The system of claim 1, wherein a sheath is disposed over at least a portion of the diaphragm to prevent brain or other tissue from impinging directly thereupon following implantation.

5. The system of claim 1, wherein implantable medical device is configured to combine the first and the second data.

6. The system of claim 1, wherein the external device is configured to combine the first and the second data.

7. The system of claim 1, wherein the implantable medical device and the external device are configured to communicate by radio frequency telemetry means.

8. The system of claim 1, wherein the external device is configured to permit programming of the implantable medical device so that the implantable medical device operates in a predetermined manner defined by the external device.

9. The system of claim 1, wherein the third data are displayed in the external device for viewing by a user.

10. The system of claim 1, wherein the capacitive pressure sensor is configured such that the output signals provided thereby drift less than about 1 mm Hg over a one week period of time.

11. The system of claim 1, wherein the capacitive pressure sensor is configured such that the output signals provided thereby drift less than about 1 mm Hg over a one month period of time.

12. The system of claim 1, wherein the capacitive pressure sensor is configured such that the output signals provided thereby drift less than about 1 mm Hg over a one year period of time.

13. The system of claim 1, further comprising means for calculating intracranial temperature on the basis of signals provided by the intracranial sensor.

14. The system of claim 1, further comprising means for delivering a therapy to the patient upon detecting a predetermined intracranial condition or state of the patient.

* * * * *

UNITED STATES PATENT AND TRADEMARK OFFICE
CERTIFICATE OF CORRECTION

PATENT NO. : 6,248,080 B1
DATED : June 19, 2001
INVENTOR(S) : Miesel et al.

It is certified that error appears in the above-identified patent and that said Letters Patent is hereby corrected as shown below:

<u>Title page,</u>
Item [74], *Attorney, Agent or Firm*, after "*Girma Wolde-Michael*" please insert
-- *Thomas F. Woods* and --.

Signed and Sealed this

Ninth Day of April, 2002

Attest:

Attesting Officer

JAMES E. ROGAN
*Director of the United States Patent and Trademark Office*